(12) United States Patent
Yamada

(10) Patent No.: US 11,340,170 B2
(45) Date of Patent: *May 24, 2022

(54) FLUORESCENT IMAGE ANALYZER, ANALYZING METHOD, AND PRETREATMENT EVALUATION METHOD

(71) Applicant: Sysmex Corporation, Kobe (JP)

(72) Inventor: Kazuhiro Yamada, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/061,255

(22) Filed: Oct. 1, 2020

(65) Prior Publication Data
US 2021/0025826 A1  Jan. 28, 2021

Related U.S. Application Data

(63) Continuation of application No. 16/514,789, filed on Jul. 17, 2019, now Pat. No. 10,852,238, which is a
(Continued)

(30) Foreign Application Priority Data

May 31, 2016 (JP) .................. 2016-109005
Mar. 10, 2017 (JP) .................. 2017-045666

(51) Int. Cl.
*G01N 21/64* (2006.01)
*G01N 15/14* (2006.01)
(Continued)

(52) U.S. Cl.
CPC ....... *G01N 21/6456* (2013.01); *G01N 15/147* (2013.01); *G01N 15/1434* (2013.01);
(Continued)

(58) Field of Classification Search
CPC .................................. G01N 21/6456
(Continued)

(56) References Cited

U.S. PATENT DOCUMENTS 4,786,165 A   11/1988  Yamamoto
5,534,703 A    7/1996  Kambara et al.
(Continued)

FOREIGN PATENT DOCUMENTS

CN       1103951 A    6/1995
CN    101228283 A    7/2008
(Continued)

OTHER PUBLICATIONS

"Questions Concerning Fluorescence In Situ Hybridization (FISH)", *Fluorescence In Situ Hybridization (FISH)*, 2015, 22 pages (with English language translation).
(Continued)

*Primary Examiner* — Tarifur R Chowdhury
*Assistant Examiner* — Omar H Nixon
(74) *Attorney, Agent, or Firm* — Crowell & Moring LLP

(57) ABSTRACT

A fluorescence image analyzer, analyzing method, and pretreatment evaluation method capable of determining with high accuracy whether a sample is positive or negative are provided. A pretreatment part performs pretreatment including a step of labeling a target site with a fluorescent dye to prepare a sample. A fluorescence image analyzer measures and analyzes the sample. The fluorescent image analyzer includes light sources to irradiate light on the sample, imaging part to capture the fluorescent light given off from the sample irradiated by light, and processing part for processing the fluorescence image captured by the imaging part. The processing part extracts the bright spot of fluorescence generated from the fluorescent dye that labels the target site from the fluorescence image for each of a plurality
(Continued)

of cells included in the sample, and generates information used for determining whether the sample is positive or negative based on the bright spots extracted for each of the plurality of cells.

20 Claims, 20 Drawing Sheets

Related U.S. Application Data continuation of application No. 15/608,380, filed on May 30, 2017, now Pat. No. 10,401,289.

(51) Int. Cl.
| | |
|---|---|
| G06T 7/00 | (2017.01) |
| G01N 33/483 | (2006.01) |
| G01N 15/00 | (2006.01) |
| G01N 15/10 | (2006.01) |

(52) U.S. Cl.
CPC ..... *G01N 15/1436* (2013.01); *G01N 15/1459* (2013.01); *G01N 15/1475* (2013.01); *G01N 21/6428* (2013.01); *G01N 21/6458* (2013.01); *G01N 33/4833* (2013.01); *G06T 7/0012* (2013.01); *G01N 2015/0065* (2013.01); *G01N 2015/1006* (2013.01); *G01N 2015/144* (2013.01); *G01N 2021/6419* (2013.01); *G01N 2021/6421* (2013.01); *G01N 2021/6439* (2013.01); *G01N 2021/6441* (2013.01); *G01N 2021/6478* (2013.01); *G01N 2201/06113* (2013.01); *G01N 2201/12* (2013.01); *G06T 2207/10056* (2013.01); *G06T 2207/10064* (2013.01); *G06T 2207/30024* (2013.01)

(58) Field of Classification Search
USPC .......................................................... 435/34
See application file for complete search history.

(56) References Cited

U.S. PATENT DOCUMENTS

| | | | |
|---|---|---|---|
| 5,726,009 | A | 3/1998 | Connors |
| 6,025,126 | A | 2/2000 | Westbrook |
| 6,211,955 | B1 | 4/2001 | Basiji et al. |
| 6,927,401 | B1 | 8/2005 | Palo |
| 2003/0186210 | A1 | 10/2003 | Fujino |
| 2005/0070005 | A1 | 3/2005 | Keller |
| 2006/0073509 | A1 | 4/2006 | Kilpatrick et al. |
| 2006/0094868 | A1 | 5/2006 | Giuliano |
| 2008/0261295 | A1 | 10/2008 | Butler |
| 2009/0027676 | A1 | 1/2009 | Model |
| 2009/0303209 | A1 | 12/2009 | Teng |
| 2010/0321484 | A1 | 12/2010 | Kishima |
| 2011/0025880 | A1 | 2/2011 | Nandy |
| 2011/0117025 | A1 | 5/2011 | Dacosta |
| 2011/0136152 | A1 | 6/2011 | Lin |
| 2011/0212090 | A1 | 9/2011 | Pedersen |
| 2011/0254943 | A1 | 10/2011 | Ozinsky |
| 2012/0003711 | A1 | 1/2012 | Tseng |
| 2012/0062722 | A1* | 3/2012 | Sase .................. G01N 21/6458 348/79 |
| 2012/0156246 | A1 | 6/2012 | Bamdad |
| 2013/0171621 | A1 | 7/2013 | Luo et al. |
| 2013/0252272 | A1 | 9/2013 | Moertelmaier |
| 2013/0337471 | A1 | 12/2013 | Nie |
| 2014/0030729 | A1 | 1/2014 | Basiji |
| 2014/0120556 | A1 | 5/2014 | Moll |
| 2014/0131592 | A1 | 5/2014 | Kishima |
| 2014/0210841 | A1 | 7/2014 | Song |
| 2014/0322276 | A1 | 10/2014 | Bernard |
| 2015/0083320 | A1 | 3/2015 | Putnam |
| 2015/0125884 | A1 | 5/2015 | Budin |
| 2015/0132766 | A1 | 5/2015 | Yasuda |
| 2015/0299784 | A1 | 10/2015 | Fan |
| 2015/0361449 | A1 | 12/2015 | Too |
| 2015/0362716 | A1 | 12/2015 | Kei |
| 2016/0186210 | A1 | 6/2016 | Verdin |
| 2016/0202465 | A1 | 7/2016 | Sase |
| 2016/0289669 | A1 | 10/2016 | Fan |
| 2017/0107495 | A1 | 4/2017 | Itescu |
| 2017/0342470 | A1 | 11/2017 | Gouda |
| 2017/0370920 | A1 | 12/2017 | Akama |

FOREIGN PATENT DOCUMENTS

| | | |
|---|---|---|
| EP | 1744145 | 1/2007 |
| JP | 2003-520954 A | 7/2003 |
| JP | 2005-515408 A | 5/2005 |
| JP | 2008-283989 A | 11/2008 |
| JP | 2008292283 A | 12/2008 |
| JP | 2011-523847 A | 8/2011 |
| JP | 2014-502493 A | 2/2014 |
| JP | 2016-507229 A | 3/2016 |
| WO | 01/53784 A1 | 7/2001 |
| WO | WO 02/093130 A2 | 11/2002 |
| WO | 2006/036735 A2 | 4/2006 |

OTHER PUBLICATIONS

Hasegawa, T., "Role of Molecular Pathology Diagnosis in Soft Tissue Sarcoma", *State of Molecular Pathology Diagnosis*, 2008, 24 pages (with English language translation).
William E. Ortyn et al: "Extended Depth of Field Imaging for High Speed Cell Analysis", NIH Public Access Author Manuscript, International Society for Analytical Cytology, vol. 71A, No. 4, Feb. 5, 2007, pp. 215-231.
Gábor Pajor et al: "State-of-the-Art FISHing: Automated Analysis of Cytogenetic Aberrations in Interphase Nuclei", NIH Public Access Author Manuscript, International Society for Advancement of Cytometry, vol. 81A, No. 8, Jun. 13, 2012, pp. 649-663.
The Communication pursuant to Article 94(3) EPC dated Sep. 17, 2020 in a counterpart European patent application No. 17172419.8.
The Japanese Office Action dated Feb. 9, 2021 in a counterpart Japanese patent application No. 2017-202960.
The Japanese Office Action dated Feb. 9, 2021 in a counterpart Japanese patent application No. 2017-202959.
The Japanese Decision of Refusal dated Sep. 28, 2021 in a counterpart Japanese patent application No. 2017-202959.
The Chinese Office Action dated May 25, 2021 in a counterpart Chinese patent application No. 201710428315.X.
Summons to attend oral proceedings pursuant to Rule 115(1) EPC dated Mar. 11, 2022 in a counterpart European patent application No. 17172419.8.

\* cited by examiner

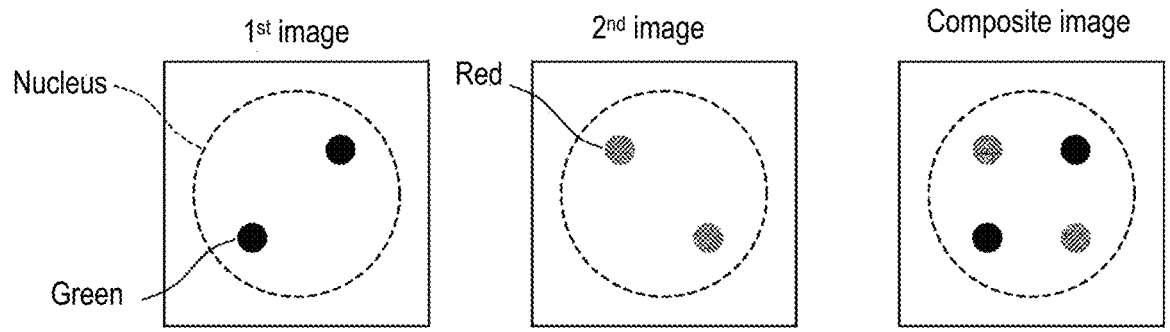
FIG. 3A Negative pattern
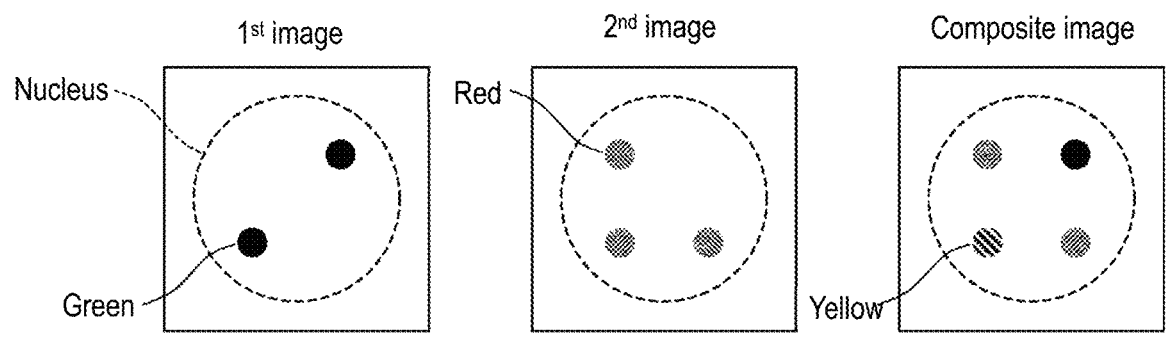
FIG. 3B Positive pattern 1
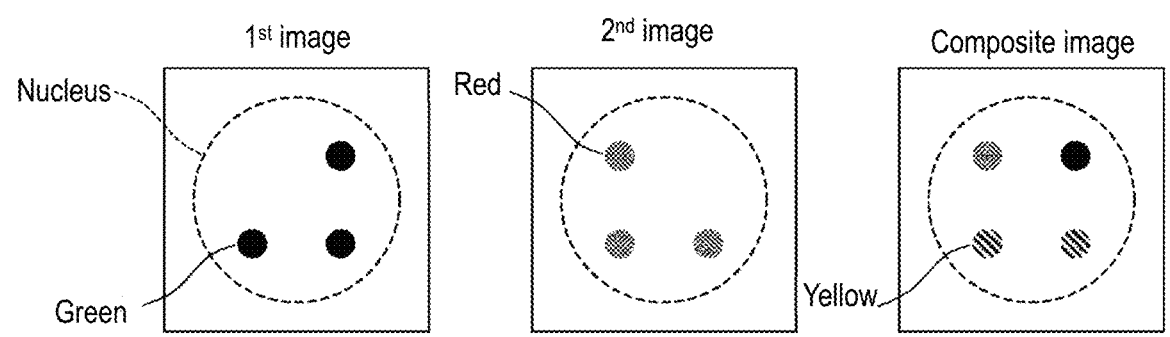
FIG. 3C Positive pattern 2
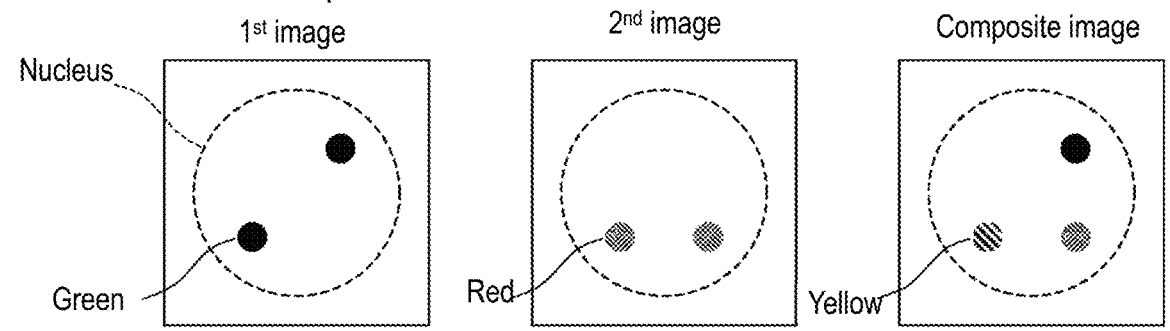
FIG. 3D Positive pattern 3

| No. | 1st index | | | | | | | Proportion of bright spot negative pattern and positive patterns 1 to 3 |
|---|---|---|---|---|---|---|---|---|
| | Control factor | | | | | | | |
| | A | B | C | D | E | F | G | |
| | Heat denaturation temp | Heat denaturation time | Heat denaturation method | Hybridization temp | Probe amount | Wash solution temp | Wash solution salt concentration | |
| 1 | ... | ... | ... | ... | ... | ... | ... | 64% |
| 2 | ... | ... | ... | ... | ... | ... | ... | 52% |
| 3 | ... | ... | ... | ... | ... | ... | ... | 57% |
| 4 | ... | ... | ... | ... | ... | ... | ... | 60% |
| 5 | 92 | 5 | Method 2 | 37 | ×2 | 70 | ×0.4 | 68% |
| 6 | ... | ... | ... | ... | ... | ... | ... | 57% |
| 7 | ... | ... | ... | ... | ... | ... | ... | 48% |
| 8 | ... | ... | ... | ... | ... | ... | ... | 31% |

FIG. 4

FIG. 11B
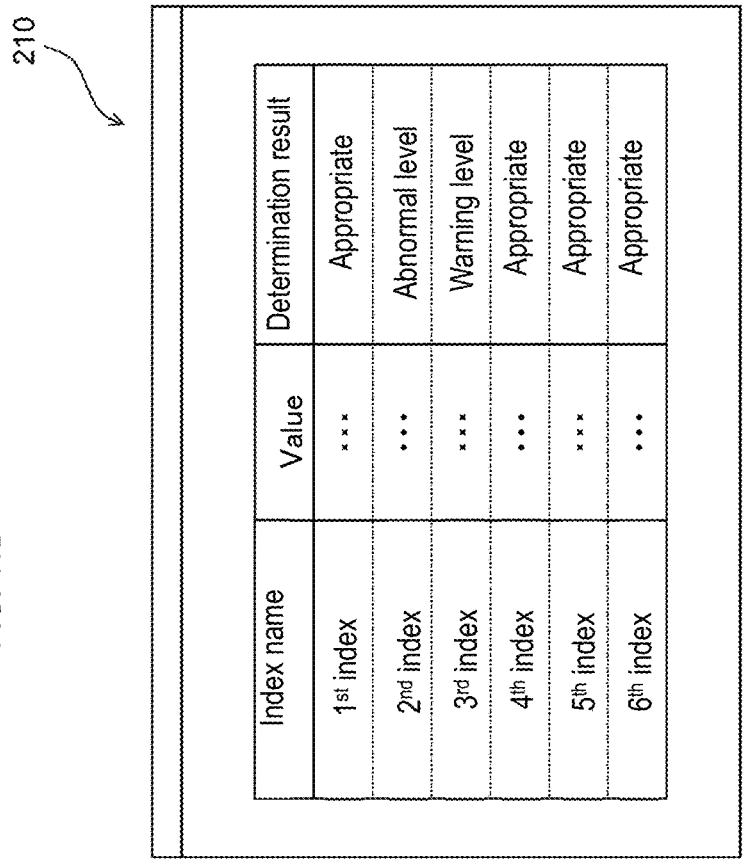
FIG. 11A 1st embodiment
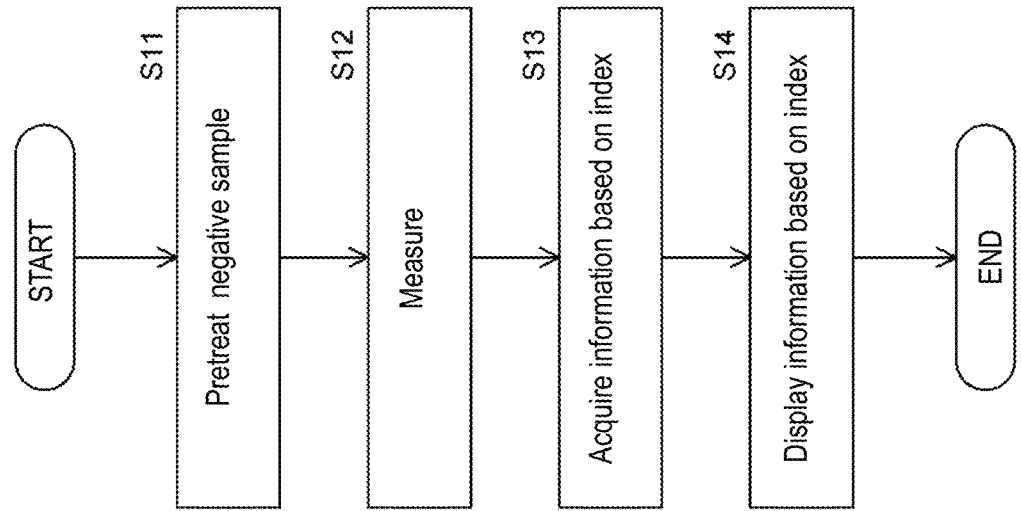

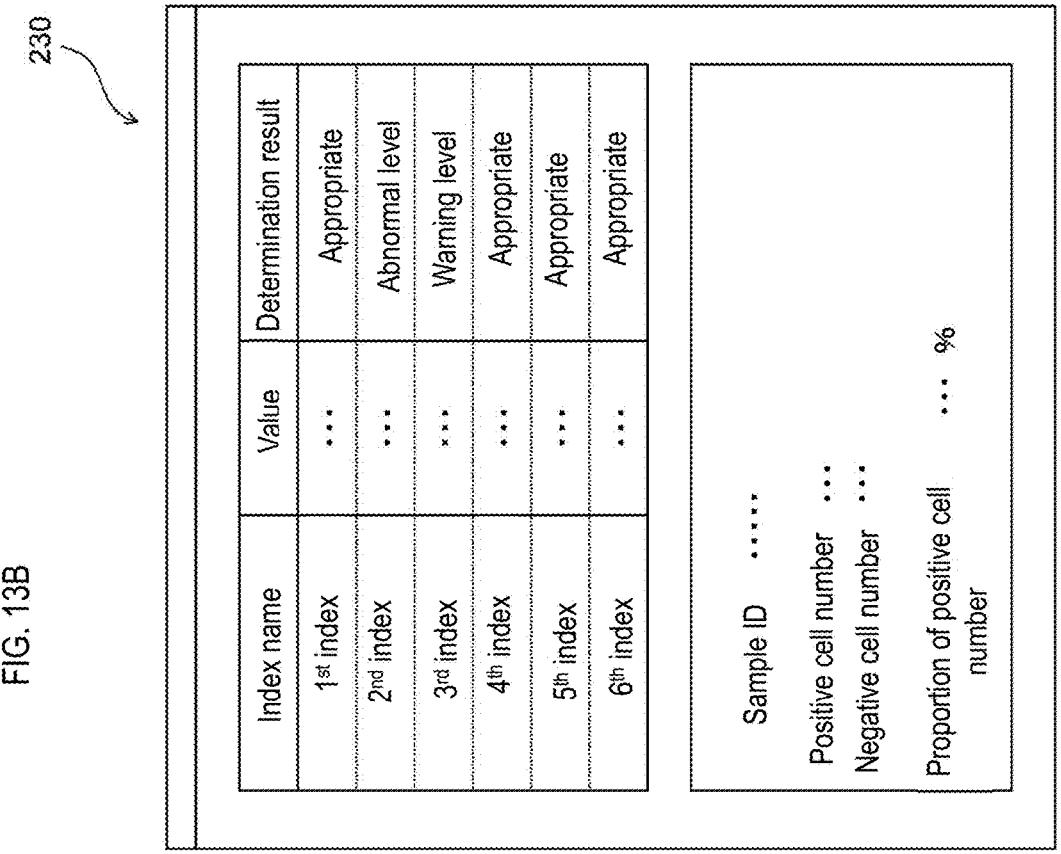
FIG. 13B
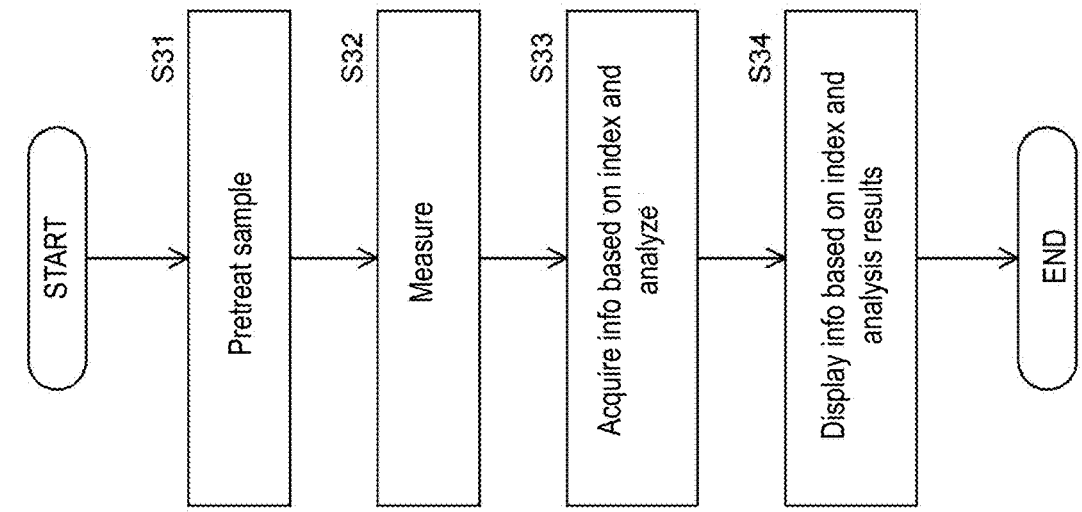
FIG. 13A 2nd embodiment

FIG. 14A 3rd embodiment

| Date and time | Sample ID | 1st image | 2nd image | 3rd image | Bright field image |
|---|---|---|---|---|---|
| ..... | ..... | ... | ... | ... | ... |
| ..... | ..... | ... | ... | ... | ... |
| ..... | ..... | ... | ... | ... | ... |

| Date and time | Sample ID | 1st index | 2nd index | 3rd index | 4th index | 5th index | 6th index |
|---|---|---|---|---|---|---|---|
| ..... | ..... | ... | ... | ... | ... | ... | ... |
| ..... | ..... | ... | ... | ... | ... | ... | ... |
| ..... | ..... | ... | ... | ... | ... | ... | ... |

12b

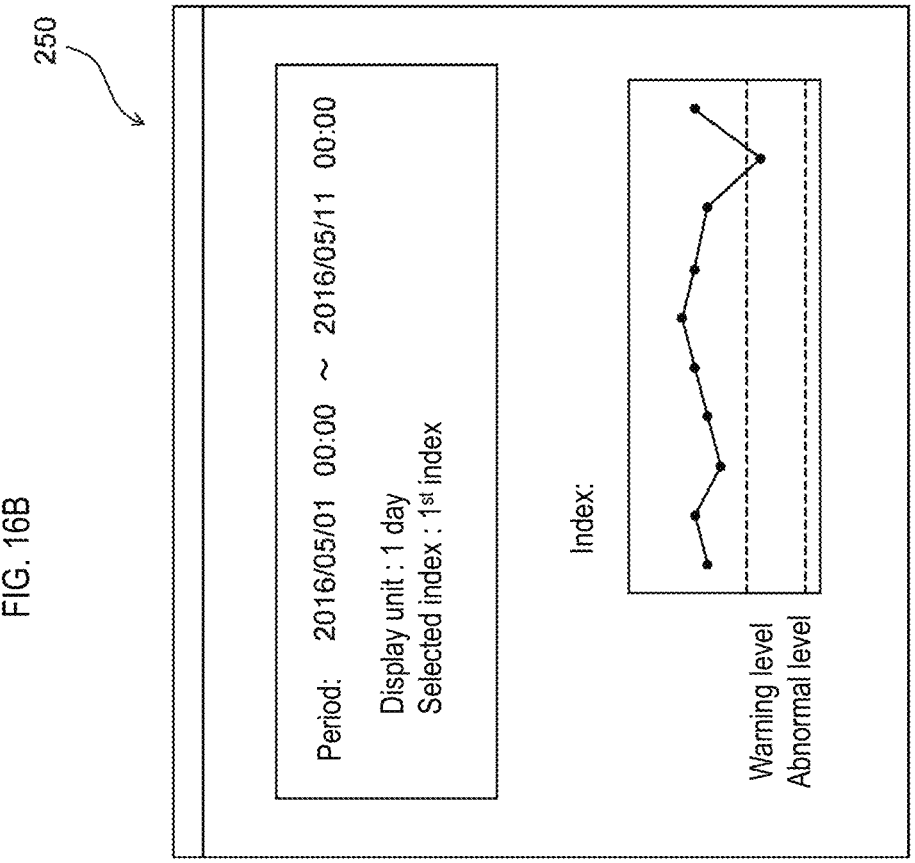
FIG. 16B
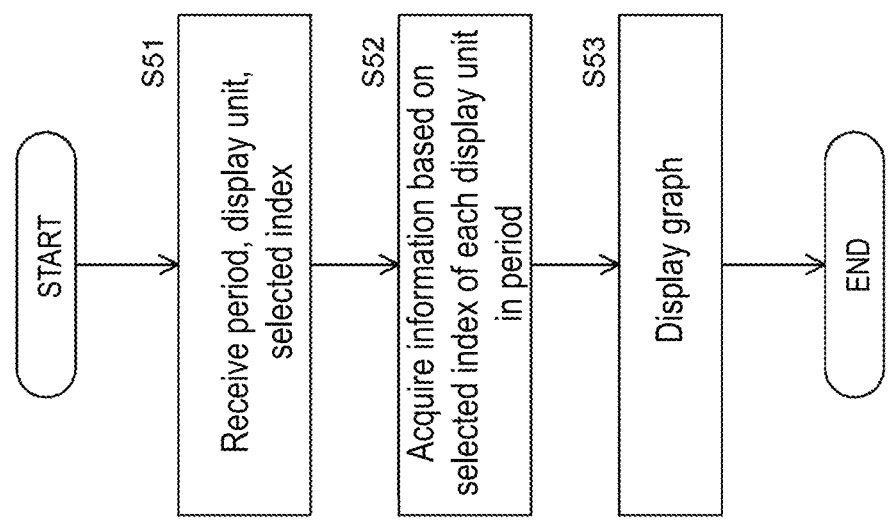
FIG. 16A 4th embodiment

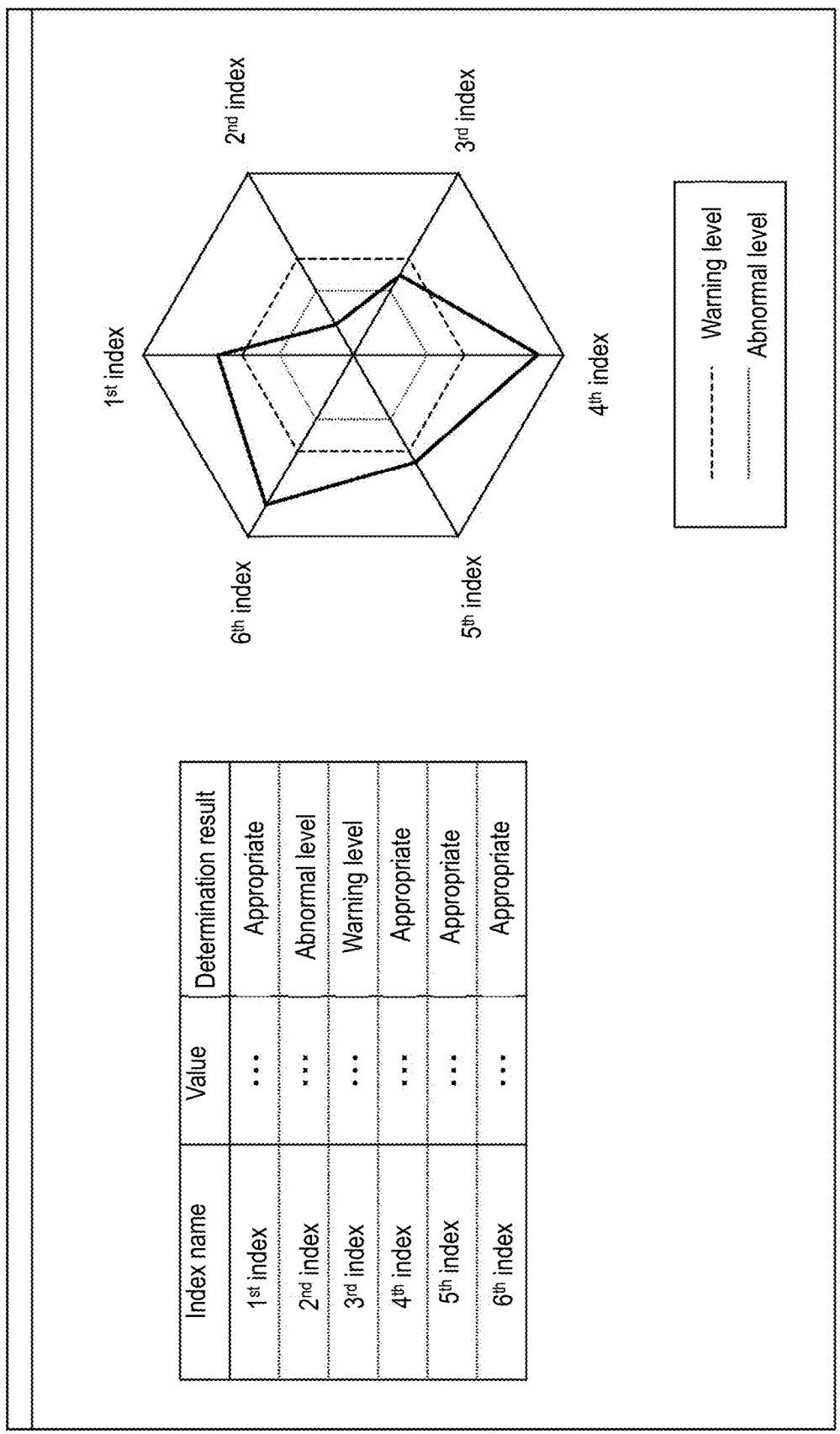
FIG. 17 8th embodiment

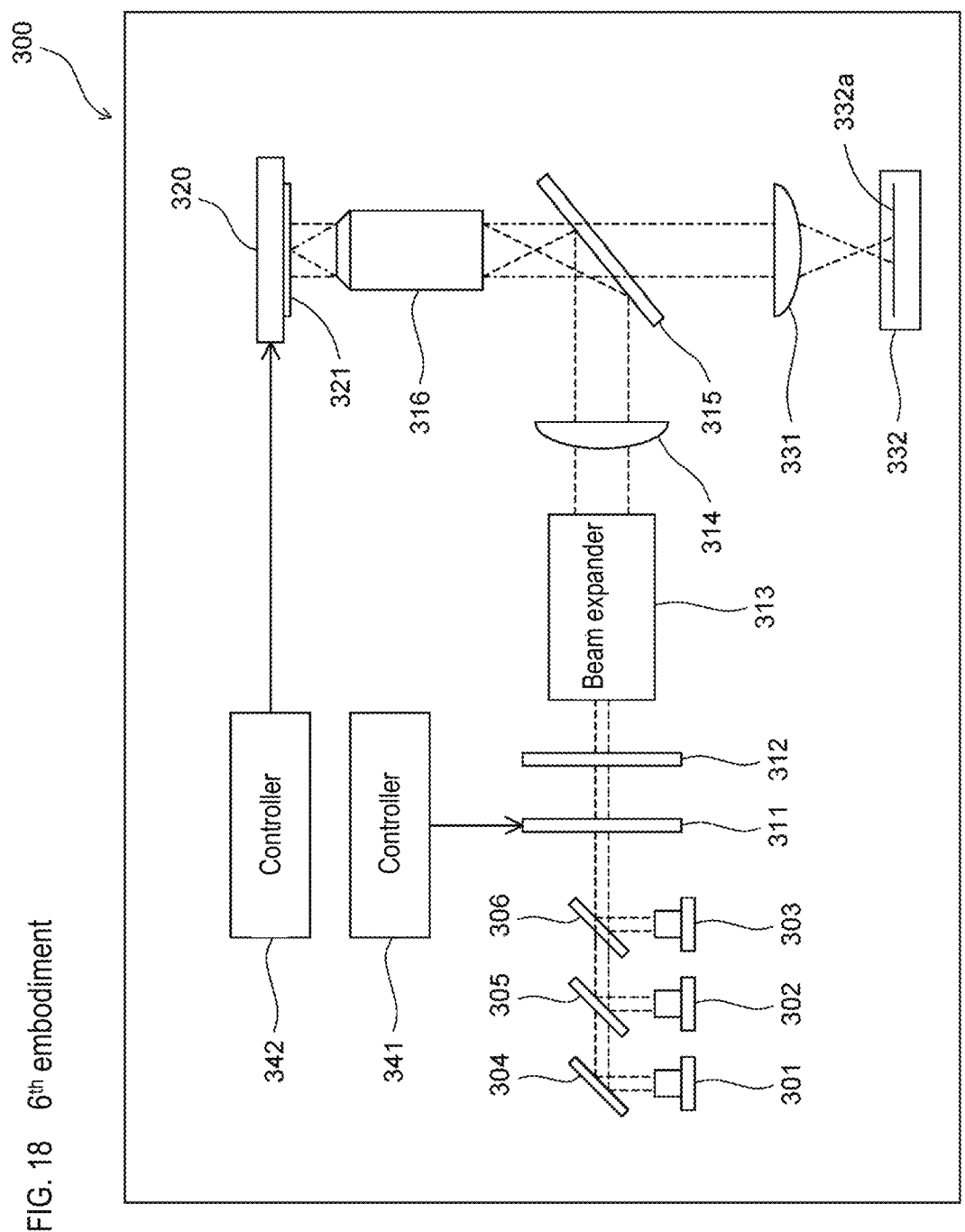
FIG. 18  6th embodiment

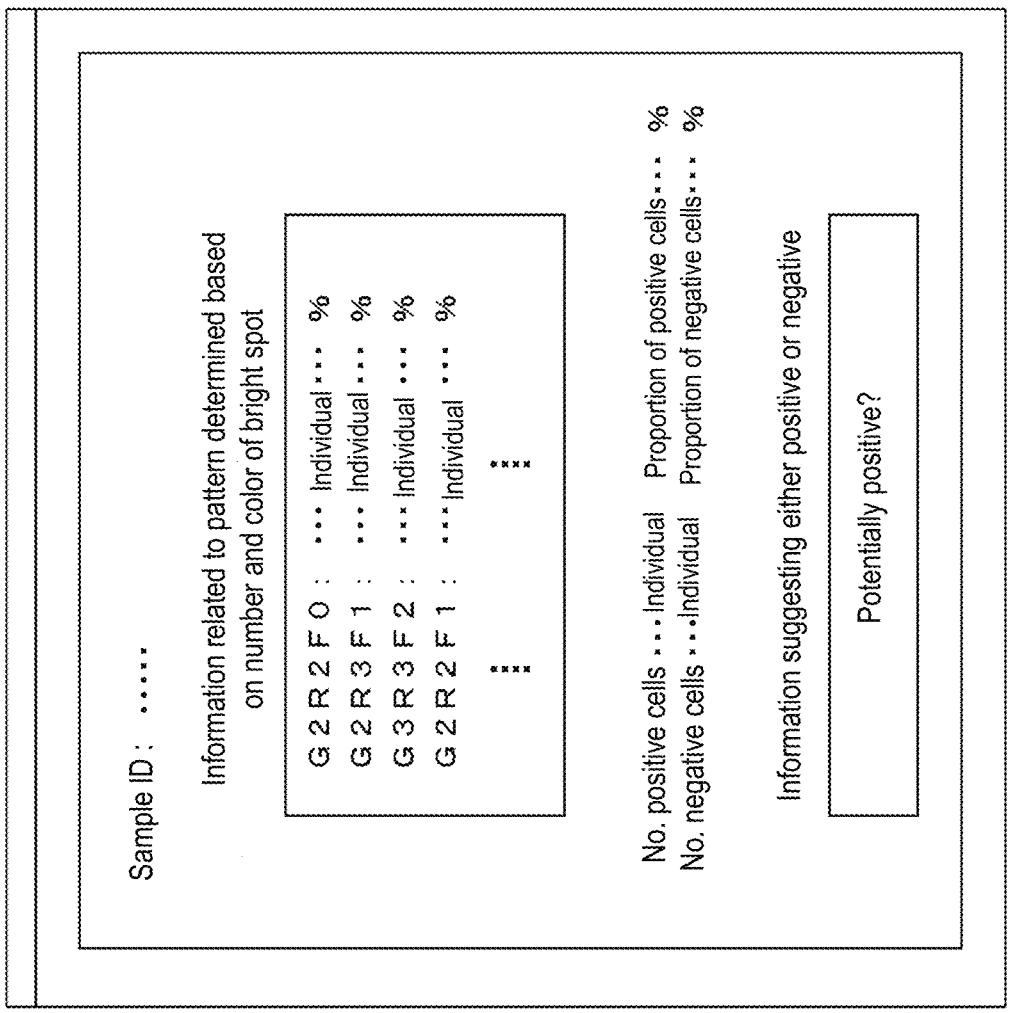

FIG. 20A 8th embodiment

| Bright spot pattern | Determination |
|---|---|
| G2R2F0 | Negative |
| G2R3F1 | Positive |
| G3R3F2 | Positive |
| G2R2F1 | Positive |

FIG. 20B

Sample ID : ......

Information related to pattern determined based on number and color of bright spot G2R2F0 : ···· Individual ··· %
G2R3F1 : ···· Individual ··· %
G3R3F2 : ···· Individual ··· %
G2R2F1 : ···· Individual ··· %
····

No. positive cells ····Individual   Proportion of positive cells··· %
No. negative cells ···Individual   Proportion of negative cells··· %

Information suggesting either positive or negative

Potentially positive?

FLUORESCENT IMAGE ANALYZER, ANALYZING METHOD, AND PRETREATMENT EVALUATION METHOD

CROSS REFERENCE TO RELATED APPLICATIONS

This application is a continuation under 35 U.S.C. § 120 of U.S. application Ser. No. 16/514,789, filed on Jul. 17, 2019, which is a continuation of U.S. application Ser. No. 15/608,380, filed on May 30, 2017, entitled "FLUORESCENT IMAGE ANALYZER, ANALYZING METHOD, AND PRETREATMENT EVALUATION METHOD," which claims priority from prior Japanese Patent Application No. 2016-109005, filed on May 31, 2016, entitled "FLUORESCENT IMAGE ANALYZER AND PRETREATMENT EVALUATION METHOD," and prior Japanese Patent Application No. 2017-045666, filed on Mar. 10, 2017, entitled "FLUORESCENT IMAGE ANALYZER, ANALYZING METHOD, AND PRETREATMENT EVALUATION METHOD," the entire contents of each of which are incorporated herein by reference.

FIELD OF THE INVENTION

The invention relates to a fluorescent image analyzer, analyzing method, and pretreatment evaluation method.

BACKGROUND

Japanese Patent Application Publication No. 2005-515408 describes a cell treatment method when a flow cytometer or the like is applied for detection by the fluorescence in situ hybridization method (FISH method). According to the FISH method, cells are stained by pretreatment in which a labeled probe is hybridized with a DNA sequence region to be detected in a cell, and the fluorescence generated due to the labeled probe is detected so as to detect the abnormal cells.

SUMMARY OF THE INVENTION

For example, it is necessary to detect abnormal cells by observing a huge number of cells such as 1,000 to 10,000 cells when trying to accurately determine whether the collected sample is positive or negative for a specific disease using the above-described method for detecting abnormal cells. In this case, it becomes difficult to maintain the accuracy of determining whether the sample is positive or negative because the burden increases on the operator detecting abnormal cells, and the detection of abnormal cells depends on the senses of the operator.

A first aspect of the invention relates to a fluorescence image analyzer for carrying out a pretreatment including a step of labeling a target site with a fluorescent dye and measuring and analyzing the prepared sample. The fluorescence image analyzer of this aspect includes light sources to irradiate light on the sample, an imaging part to capture the fluorescent light given off from the sample irradiated by light, and a processing part for processing the fluorescence image captured by the imaging part. The processing part extracts the bright spot of fluorescence generated from the fluorescent dye that labels the target site from the fluorescence image for each of a plurality of cells included in the sample, and generates information used for determining whether the sample is positive or negative based on the bright spots extracted for each of the plurality of cells.

A second aspect of the invention relates to a fluorescence image analyzer for carrying out a pretreatment including a step of labeling a target site with a fluorescent dye and measuring and analyzing the prepared sample. The fluorescence image analyzer of this aspect includes light sources to irradiate light on the sample, an imaging part to capture the fluorescent light given off from the sample irradiated by light, and a processing part for processing the fluorescence image captured by the imaging part. The processing part extracts the bright spot of fluorescence generated from the fluorescent dye that labels the target site from the fluorescence image for each of a plurality of cells included in the sample, and generates information used for determining whether the sample is positive or negative based on the bright spots extracted for each of the plurality of cells.

A third aspect of the invention relates to analyzing method for analyzing a sample prepared in a pretreatment including a step of labeling a target site with a fluorescent dye. The analyzing method of this aspect includes a step of irradiating light on a sample prepared in pretreatment, a step of imaging fluorescence given off from the sample irradiation with light, a step of extracting a bright spot of fluorescence produced by the fluorescent dye labeling the target site from the fluorescence image for each of a plurality of cells included in the sample, and a step of generating information used to determine whether the sample is positive or negative based on the bright spots extracted for each of the plurality of cells.

A fourth aspect of the invention is an analyzing method for samples including a plurality of cells having a target site labeled with a fluorescent dye. The analyzing method of this aspect includes a step of extracting a pattern of bright spots of fluorescence generated from a fluorescent dye from each fluorescence image of a plurality of cells, a step of classifying each of the plurality of cells based on a pattern of bright spots, and a step of generating information used for determining whether the sample is positive or negative based on the classification result of the cells.

A fifth aspect of the invention relates to a fluorescence image analyzer for carrying out a pretreatment including a step of labeling a target site with a fluorescent dye and measuring and analyzing the prepared sample. The fluorescence image analyzer of this aspect includes light sources to irradiate light on the sample, an imaging part to capture the fluorescent light given off from the sample irradiated by light, and a processing part for processing the fluorescence image captured by the imaging part. The processing part extracts a bright spot of fluorescence generated from the fluorescent dye that labels the target site from the fluorescence image, acquires an index reflecting the state of the bright spot based on the extracted bright spot, and determines whether pretreatment is appropriate based on the acquired index.

A sixth aspect of the invention relates to a fluorescence image analyzer for carrying out a pretreatment including a step of labeling a target site with a fluorescent dye and measuring and analyzing the prepared sample. The fluorescence image analyzer of this aspect includes light sources to irradiate light on the sample, an imaging part to capture the fluorescent light given off from the sample irradiated by light, and a processing part for processing the fluorescence image captured by the imaging part. The processing part extracts a bright spot of fluorescence generated from the fluorescent dye that labels the target site from the fluorescence image, acquires an index reflecting the state of the bright spot based on the extracted bright spot, and causes information based on the acquired index to be shown on the display part.

A seventh aspect of the invention is an evaluation method for pretreatment of cell analysis including a step of labeling a target site with a fluorescent dye. The evaluation method for pretreatment of this aspect includes a step of irradiating light on a sample prepared in the pretreatment, a step of capturing the fluorescence generated from the sample irradiated with light, a step of extracting the bright spot of fluorescent light generated from the fluorescent dye that labels the target site from the fluorescence image, a step of acquiring an index reflecting the state of the bright point based on the extracted bright spot.

According to the invention, whether a sample is positive or negative can be determined with high accuracy.

BRIEF DESCRIPTION OF THE DRAWINGS

FIGS. 3A through 3D schematically show respective examples of the bright spot arrangements of a negative pattern, positive pattern 1, positive pattern 2, and positive pattern 3 of the embodiment;

FIG. 4 illustrates a first index of the embodiment;
FIG. 11A is a flow chart showing the process of displaying the determination results of whether pretreatment is appropriate according to the first embodiment;

FIG. 11B schematically shows the structure of a screen displayed on the display part of the first embodiment;

FIG. 13A is a flow chart showing the process of displaying the determination results of whether pretreatment is appropriate and the analysis results according to a second embodiment;

FIG. 13B schematically shows the structure of a screen displayed on the display part of the second embodiment;

FIG. 14A and FIG. 14B conceptually show the structure of a database stored in the memory part of a third embodiment;

FIG. 16A is a flow chart showing the process of displaying the determination results of whether pretreatment is appropriate according to a fourth embodiment; FIG. 16B schematically shows the structure of a screen displayed on the display part of the fourth embodiment;

FIG. 17 schematically shows the structure of a screen displayed on the display part of a fifth embodiment;

FIG. 18 schematically shows the structure of the imaging part of a sixth embodiment;

FIG. 20A schematically shows the bright spot patterns stored in the memory part and the determinations associated with the bright spot patterns of an eighth embodiment; and FIG. 20B schematically shows the structure of a screen displayed on the display part of the eighth embodiment.

DETAILED DESCRIPTION OF THE PREFERRED EMBODIMENTS

The following embodiment is an application of the present invention applied to an apparatus for measuring and analyzing a sample prepared in a pretreatment including a step of hybridizing a nucleic acid probe labeled with a fluorescent dye and a target site in a nucleic acid. Specifically, in the following embodiment, the target site in the nucleic acid is the BCR gene on chromosome 22 and the ABL gene on chromosome 9, and cells with translocation between chromosome 22 and chromosome 9 found in chronic myeloid leukemia are detected as abnormal cells based on the FISH method. That is, in the following embodiment, a cell in which a BCR gene or ABL gene is translocated to generate a BCR-ABL fusion gene is detected as an abnormal cell. In the following embodiments, the cells to be detected are white blood cells in the blood sample.

Apparatus Structure

Figure 1:
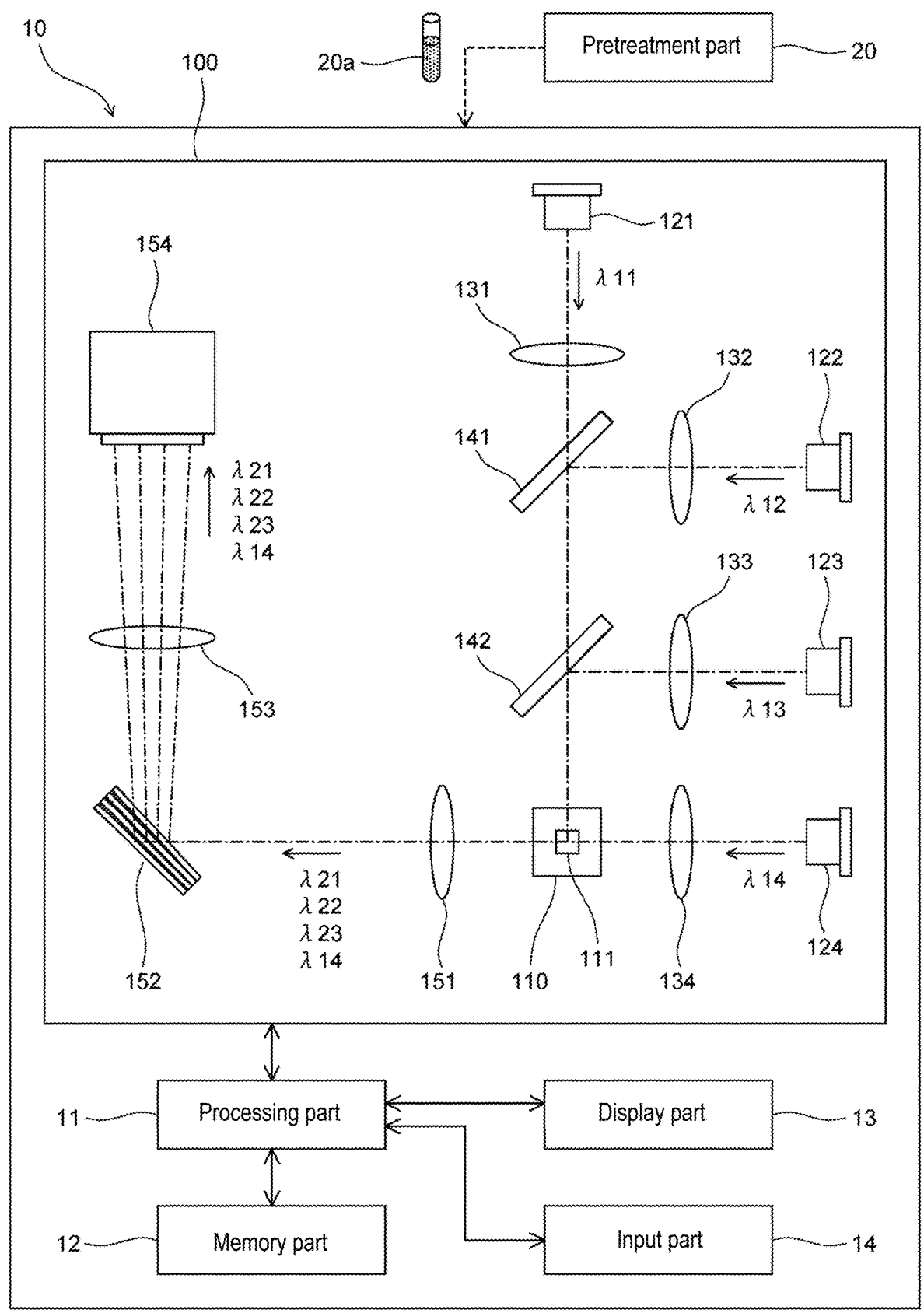
FIG. 1 schematically shows the structures of the fluorescence image analyzer and pretreatment part of the embodiment.

As shown in FIG. 1, the fluorescence image analyzer 10 measures and analyzes a sample 20a prepared by pretreatment by the pretreatment part 20. The operator performs processing such as centrifugal separation on blood specimens collected from a subject and extracts leukocytes as detection target cells. In the extraction of white blood cells, leukocytes may be extracted by hemolyzing other blood cells with a hemolytic agent instead of centrifugation. The pretreatment part 20 includes a mixing container for mixing the reagent and the sample subjected to treatment such as centrifugal separation, a dispensing part for dispensing the sample and reagent to the mixing container, and a heating part to heat the mixing container. The pretreatment part 20 carries out a pretreatment including a step of labeling the target site of the detection target cells collected from the subject with the fluorescent dye, and a step of specifically staining the nucleus of the cell with the dye by nuclear staining to prepare sample 20a. Specifically, in the step of labeling the target site with the fluorescent dye, a nucleic acid probe labeled with the fluorescent dye and the target site in the nucleic acid are hybridized.

The nucleic acid probe that hybridizes with the BCR gene is labeled with a first fluorescent dye that produces fluorescence with a wavelength $\lambda 21$ upon irradiation with excitation light of wavelength $\lambda 11$. In this way the BCR gene is labeled with the first fluorescent dye. The nucleic acid probe that hybridizes with the ABL gene is labeled with a second fluorescent dye that produces fluorescence with a wavelength $\lambda 22$ upon irradiation with excitation light of wavelength $\lambda 12$. In this way the ABL gene is labeled with the second fluorescent dye. The nucleus is dyed with a dye for nuclear staining which produces fluorescence of wavelength $\lambda 23$ by irradiation with excitation light of wavelength $\lambda 13$.

More specifically, the pretreatment part 20 includes a treatment for immobilizing the cells so that the cells do not contract due to dehydration, a membrane permeation treatment for opening a hole of a size sufficient to introduce the nucleic acid probe into the cell, a heat denaturation treatment to add heat to the cells, a treatment of hybridizing a target site and a nucleic acid probe, a washing treatment to remove unnecessary nucleic acid probe from a cell, and a treatment to stain a nucleus.

The fluorescence image analyzer 10 includes an imaging unit 100, a processing part 11, a memory part 12, a display part 13, and an input part 14. The imaging unit 100 includes a flow cell 110, light sources 121 to 124, condenser lenses 131 to 134, dichroic mirrors 141 and 142, a condenser lens 151, an optical unit 152, a condenser lens 153, an imaging part 154. The sample 20a flows through the flow path 111 of the flow cell 110.

The light sources 121 to 124 irradiate light on the sample 20a flowing through the flow cell 110. The light sources 121 to 124 are configured by a semiconductor laser light source. The light emitted from the respective light sources 121 to 124 is laser light of wavelengths $\lambda 11$ to $\lambda 14$. The condenser lenses 131 to 134 condense the light from the respective light sources 121 to 124. The dichroic mirror 141 transmits light of wavelength $\lambda 11$ and reflects light of wavelength $\lambda 12$. The dichroic mirror 142 transmits light of wavelength $\lambda 11$ and $\lambda 12$, and reflects light of wavelength $\lambda 13$. Thus, the light of wavelengths $\lambda 11$ to $\lambda 14$ irradiate the sample flowing through the flow path 111 of the flow cell 110.

When the sample flowing through the flow cell 110 is irradiated with light having wavelengths $\lambda 11$ to $\lambda 13$, fluorescence is given off from the fluorescent dye staining the cells. Specifically, when the first fluorescent dye that labels the BCR gene is irradiated by light of wavelength $\lambda 11$, fluorescence of wavelength $\lambda 21$ is given off from the first fluorescent dye. When the second fluorescent dye that labels the ABL gene is irradiated by light of wavelength $\lambda 12$, fluorescence of wavelength $\lambda 22$ is given off from the second fluorescent dye. When the dye for nuclear staining which stains the nucleus is irradiated by light of the wavelength $\lambda 13$, fluorescence of wavelength $\lambda 23$ is given off from the dye for nuclear staining. When the sample flowing through the flow cell 110 is irradiated with light of wavelength $\lambda 14$, this light transmits through the cell. The light of wavelength $\lambda 14$ that has passed through the cell is used for generating a bright field image. In the embodiment, the wavelength $\lambda 21$ is a wavelength band of green light, wavelength $\lambda 22$ is a wavelength band of red light, and wavelength $\lambda 23$ is a wavelength band of blue light.

The condensing lens 151 collects the fluorescence of wavelengths $\lambda 21$ to $\lambda 23$ generated from the sample flowing through the flow channel 111 of the flow cell 110, and the light of wavelength $\lambda 14$ transmitted through the sample flowing through the flow channel 111 of the flow cell 110. An optical unit 152 has a configuration combining four dichroic mirrors. The four dichroic mirrors of the optical unit 152 reflect the fluorescence of the wavelengths $\lambda 21$ to $\lambda 23$ and the light of the wavelength $\lambda 14$ at slightly different angles from each other and separates them on the light receiving surface of the imaging part 154. The condenser lens 153 condenses the fluorescent light of wavelengths $\lambda 21$ to $\lambda 23$, and the light of wavelength $\lambda 14$.

The imaging part 154 is configured by a TDI (Time Delay Integration) camera. The imaging part 154 captures the fluorescence of the wavelengths $\lambda 21$ to $\lambda 23$ and the light of the wavelength $\lambda 14$ and outputs the fluorescence image corresponding to the respective fluorescence lights of wavelengths $\lambda 21$ to $\lambda 23$ and the bright field image corresponding to the light of wavelength $\lambda 14$ as image signals. Fluorescent images corresponding to the fluorescence of wavelengths $\lambda 21$ to $\lambda 23$ are hereinafter referred respectively to as "first image", "second image", and "third image".

Figure 2A:
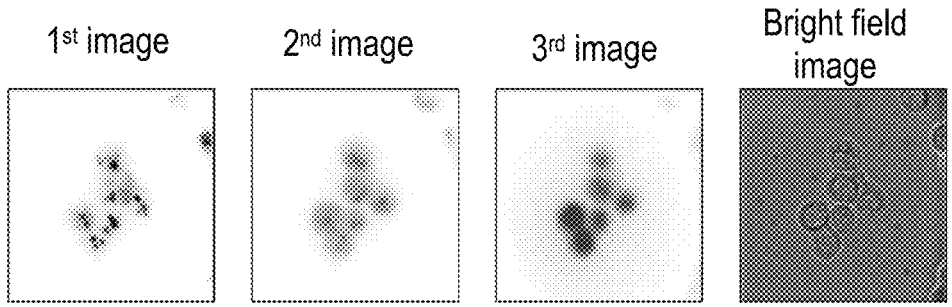
FIG. 2A shows an example of first through third images and a bright field image acquired by the fluorescence image analyzer of the embodiment.

In the example of FIG. 2A, bright spots of fluorescence of wavelength $\lambda 21$ are distributed in black dots in the first image, and bright spots of fluorescence of wavelength $\lambda 22$ are distributed in black dots in the second image, albeit somewhat thinner compared to the first image. In the third image, the nuclear region is distributed in black. In the bright-field image, the actual state of the cell can be verified. Note that each image in FIG. 2A is an image showing, as an example, a sample obtained by placing white blood cells after pretreatment on a slide glass and observing with a microscope, and the first to third images in FIG. 2A are obtained by inverting the gradation and then changing the color tone to gray. In the case where the sample 20a flowing through the flow cell 110 is imaged by the imaging part 154 as described above, the sample 20a flows through the flow path 111 with the cells mutually separated from each other, so that the fluorescence images and the bright field image are obtained for each cell.

Returning to FIG. 1, the processing part 11 is configured by a CPU. The processing part 11 also may be configured by a CPU and microcomputer. The processing part 11 performs processing of various types based on a program stored in the memory part 12. The processing part 11 is connected to the imaging unit 100, memory part 12, display part 13, and input part 14, receives signals from each part, and controls each part. The memory part 12 is configured by RAM, ROM, hard disk or the like. The display part 13 is configured by a display. The input part 14 is configured by a mouse and keyboard.

The processing part 11 processes the first to third images captured by the imaging part 154. Specifically, the processing part 11 extracts bright spots of fluorescence of wavelength $\lambda 21$ from the first image based on the fluorescent light of wavelength $\lambda 21$, and extracts bright spots of fluorescence of wavelength $\lambda 22$ from the second image based on the fluorescent light of wavelength $\lambda 22$. The processing part 11 also extracts the nuclear region from the third image based on the fluorescent light of wavelength $\lambda 23$.

The processing part 11 detects abnormal cells by determining whether the BCR gene or the ABL gene is a translocated abnormal cell for each cell based on the distribution status of the bright spots in the first image and the second image. The determination of the abnormal cell is described below referring to FIGS. 3A to 3D.

The processing part 11 also generates information used for determining whether the sample 20a is positive or negative based on the bright spots extracted for each of a plurality of cells. According to the above configuration, it is unnecessary for the operator to observe an enormous number of cells to detect abnormal cells, and detection of abnormal cells does not depend on the sense of the operator, so that the detection accuracy of abnormal cells is enhanced. Therefore, the accuracy of the information used for determining whether the sample 20a is positive or negative is increased, so that the physician can determine whether the sample 20a is positive or negative with high accuracy by referring to this information. This information is described below referring to FIG. 20B.

The extraction of the nucleus region and the extraction of the bright spot region performed by the fluorescence image analyzer 10 will be described next.

Figure 2B:
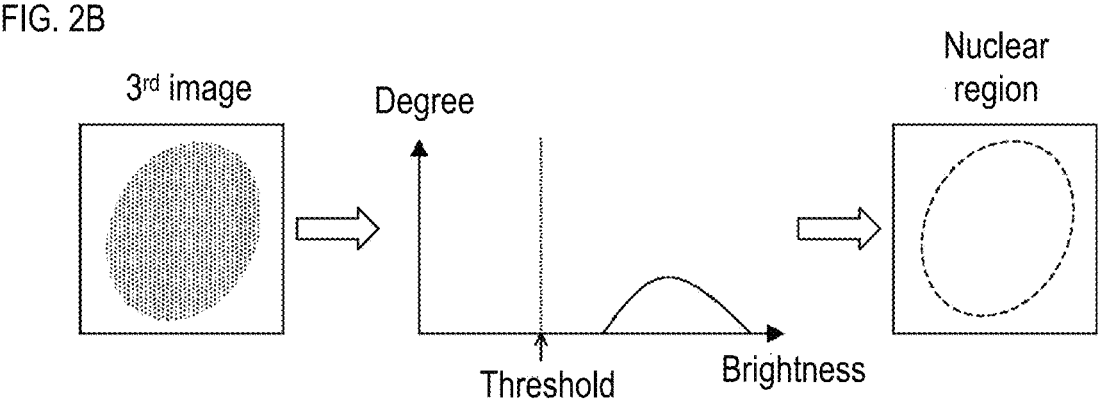
FIG. 2B illustrates the extraction of a nucleus region performed by the fluorescence image analyzer of the embodiment.
Figure 2C:
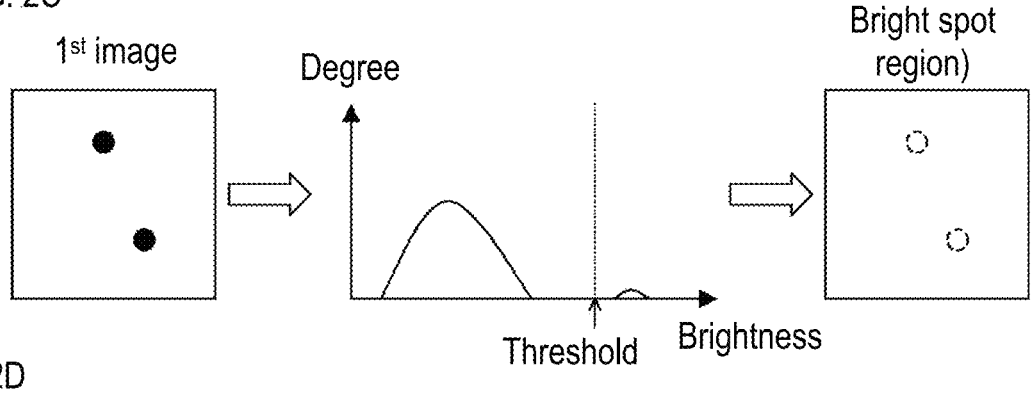
FIGS. 2C and 2D illustrate the extraction of a bright spot region performed by the fluorescence image analyzer of the embodiment.
Figure 2D:
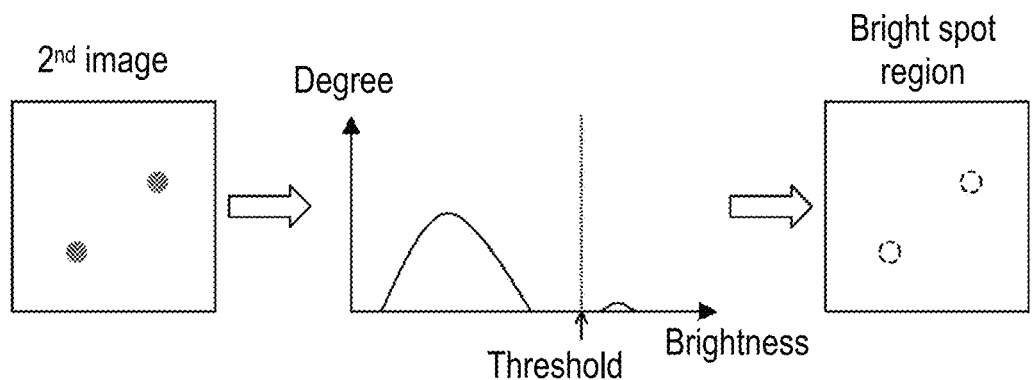

The third image shown at the left end of FIG. 2B, the first image shown at the left end of FIG. 2C, and the second image shown at the left end of FIG. 2D are acquired from the same region of sample 20a flowing through the flow cell 110.

When the third image is acquired as shown at the left end of FIG. 2B, the processing part 11 generates a graph of brightness and degree as shown in the center of FIG. 2B based on the brightness of each pixel on the third image. The degree of the vertical axis indicates the number of pixels. The processing part 11 sets the brightness threshold in this graph. The processing part 11 then extracts the range in which the pixels having a brightness larger than the threshold value are distributed as the nucleus region as indicated by the broken line at the right end of FIG. 2B Note that in the third image, when two nuclei overlap each other, the first to third images relating to the overlapped cells are excluded and are not used for determination of appropriateness of pretreatment and determination of abnormal cells.

When the first image is acquired as shown at the left end of FIG. 2C, the processing part 11 generates a graph of brightness and degree as shown in the center of FIG. 2C based on the brightness of each pixel on the first image. In this graph, the processing part 11 sets a threshold of brightness, for example, as a boundary between the bright spot and the background based on the Otsu method. The processing part 11 then extracts the range in which the pixels having a brightness larger than the threshold value are distributed as the bright spot region as indicated by the broken line at the right end of FIG. 2C. Note that when a bright spot region is extracted from the first image, a bright spot having an extremely small region, a bright spot having an extremely large region, and a bright spot not included in the nuclear region shown at the right end of FIG. 2B are excluded.

When the second image is acquired as shown at the left end of FIG. 2D, the processing part 11 generates a graph of brightness and degree as shown in the center of FIG. 2D based on the brightness of each pixel on the second image. The processing part 11 then sets the brightness threshold value in the graph, and extracts the range in which the pixels having a brightness larger than the threshold value are distributed as the bright spot region as indicated by the broken line at the right end of FIG. 2D. Note that when a bright spot region is extracted from the second image, a bright spot having an extremely small region, a bright spot having an extremely large region, and a bright spot not included in the nuclear region shown at the right end of FIG. 2B are excluded.

Note that the processing part 11 also may extract a nuclear region from the third image, and extract the bright spot region from the first image and the second image by calculation according to the procedure described above without preparing a graph as shown in the center of FIGS. 2B to 2D. The extraction of the bright spots also may be performed by determining the degree of matching between the distribution waveform of the normal bright spots and the region to be determined, and extracting the region to be determined as a bright spot when the degree of matching is high. Although the processing part 11 detects cells by extracting a nucleus region from the third image, cells also may be detected based on the bright field image. In the case where cells are detected based on the bright field image, acquisition of the third image can be omitted. Bright spot in the present embodiment means a point of small fluorescence generated in the fluorescence image. More specifically, bright spot means the point of fluorescence obtained from the fluorescent dye of the nucleic acid probe bound to the gene of the target site in the nucleus.

Determination of abnormal cells performed by the fluorescence image analyzer 10 will be described below referring to FIGS. 3A to 3D.

FIG. 3A shows an arrangement example of the bright spots of the negative pattern, and FIGS. 3B to 3D show arrangement examples of the bright spots of the positive patterns 1 to 3. Note that, in this embodiment, the arrangement pattern of the bright spots in the abnormal cell substantially coincides with any one of the positive patterns 1 to 3 shown in FIGS. 3B to 3D.

As shown in FIG. 3A, when no translocation occurs for the BCR gene and the ABL gene, there are two bright spots of fluorescence with wavelength $\lambda 21$, that is, green fluorescent light in the nucleus in the first image, and there are two bright spots of fluorescence of wavelength $\lambda 22$, that is, red fluorescent light in the nucleus in the second image. In this case, when the first image and the second image are combined, two green bright spots and two red bright spots exist in one nucleus in the composite image. In this way, when each bright spot exists as shown in FIG. 3A, the processing part 11 determines that translocation does not occur for the BCR gene and the ABL gene of this cell, that is, the cell is negative.

As shown in FIG. 3B, when a part of the ABL gene has moved to chromosome 9 due to translocation, there are two points of green fluorescence bright spots in the nucleus in the first image, and there are three red points in the nucleus of red fluorescence in the second image. In this case, when the first image and the second image are combined, one green bright spot, two red bright spots, and one yellow bright spot exist in one nucleus in the composite image. When each bright spot exists as shown in FIG. 3B, the processing part 11 determines that translocation occurs for the BCR gene and the ABL gene of this cell, that is, the cell is positive.

As shown in FIG. 3C, when a part of the BCR gene is transferred to chromosome 22 by a translocation and a part of the ABL gene is transferred to chromosome 9, three points of green fluorescence occur in the nucleus in image 1, and three points of red fluorescence lights occur in the nucleus in the second image. In this case, when the first image and the second image are combined, one green bright spot, one red bright spot, and two yellow bright spots exist in one nucleus in the composite image. When each bright spot exists as shown in FIG. 3C, the processing part 11 determines that translocation occurs for the BCR gene and the ABL gene of this cell, that is, the cell is positive.

As shown in FIG. 3D, when the ABL gene has moved to chromosome 9 due to translocation, there are two points of green fluorescence bright spots in the nucleus in the first image, and there are two points of red fluorescence bright spots in the nucleus in the second image. In this case, when the first image and the second image are combined, one green bright spot, one red bright spot, and one yellow bright spot exist in one nucleus in the composite image. When each bright spot exists as shown in FIG. 3D, the processing part 11 determines that translocation occurs for the BCR gene and the ABL gene of this cell, that is, the cell is positive.

When labeling, with fluorescent dye, a target site of a nucleic acid sequence region to be detected, in the pretreatment, for example, it is necessary to perform complex steps such as a treatment to apply heat to the cell, treatment for hybridizing a nucleic acid probe to the target site, treatment to remove unnecessary nucleic acid probe from the cell and the like. In each step of the pretreatment, there is concern that only a slight change in the treatment temperature, treatment time, reagent concentration, reagent amount and the like may break the chromosome or the target site may not be properly labeled by the nucleic acid probe. Since the analysis is performed by observing the target site based on the nucleic acid probe, unless the pretreatment is appropriately performed, there is a possibility that the analysis results will vary and the reliability of the analysis will be reduced. In addition, when an operator tries to determine the appropriateness of pretreatment, it is necessary to observe an enormous number of cells, and the suitability determination depends on the feeling of the operator, which makes it difficult to maintain determination accuracy.

It is possible to deal with the above mentioned problems if the fluorescence image analyzer 10 has the function of determining whether pretreatment is appropriate.

The processing part 11 of the fluorescence image analyzer 10 determines whether pretreatment is appropriate by acquiring an index reflecting the state of the bright spot that changes in accordance with the state of the pretreatment based on the extracted bright spot, and comparing the acquired index with a threshold value that classifies whether pretreatment is appropriate. The determination of the index and whether pretreatment is appropriate will be described later with reference to FIGS. 4 to 10.

As described above, the fluorescence image analyzer 10 acquires an index reflecting the state of the bright spot that changes in accordance with the state of the pretreatment, and whether pretreatment is appropriate is determined based on the acquired index. In this way it is possible to determine whether pretreatment is appropriate with high accuracy. In addition, when pretreatment is inappropriate, it can be an opportunity to make the pretreatment appropriate, such as reviewing the pretreatment procedure, so that the reliability of the analysis by the fluorescence image analyzer 10 can be enhanced. Compared with a case where the determination of the appropriateness of pretreatment is performed through the senses of the operator, it is possible to omit the labor of the operator and determine pretreatment appropriateness without variability.

The index reflecting the state of a bright spot that changes according to the state of pretreatment acquired by the fluorescence image analyzer 10 will be described below.

Cases when pretreatment is not performed properly include when a nucleic acid site other than the target site is fluorescently labeled by binding of a nucleic acid probe to a nucleic acid site other than the target site by so-called nonspecific binding, and when the target site is not sufficiently fluorescently labeled due to the lack of binding of the nucleic acid probe to the target site.

The inventors investigated how to properly fluorescently label the target site by setting conditions such as temperature and concentration, that is, control factors, when performing the pretreatment. In this process, the inventors found that the state of pretreatment can be determined by noticing that when the control factor is changed from the case where the state of the bright spot is most favorable, the state of the bright spot deteriorates, and determining whether the state of the degree of brightness changed from when the state of the bright spot is most favorable. Hereinafter, first to sixth indices for determining the state of pretreatment will be described.

First Index

The first index is an index focusing on the fact that the target site is properly fluorescently labeled and the number of bright spots in the first image and the second image is the presumed number if pretreatment is properly performed.

As shown in FIG. 4, the inventors performed pretreatment on standard samples, that is, negative samples, under the pretreatment conditions No. 1 to No. 8. Seven control factors A to G are set in pretreatment conditions No. 1 to No. 8. The seven control factors A to G respectively are heat denaturation temperature, heat denaturation time, heat denaturation method, hybridization temperature, probe amount, washing solution temperature, and washing solution salt concentration.

Control factor A is the temperature at which nucleic acids and nucleic acid probes are thermally denatured prior to hybridization and the units are in degrees Celsius. Control factor B is the time to thermally denature nucleic acids and nucleic acid probes, and the units are minutes. Control factor C is a method of thermally denaturing nucleic acids and nucleic acid probes. Method 2 is a method in which thermal denaturation of a nucleic acid and thermal denaturation of a nucleic acid probe are carried out at the same time. Control factor D is the temperature at which the nucleic acid and the nucleic acid probe are hybridized, and the units are in degrees Celsius. Control factor E is the magnification of the amount of nucleic acid probe relative to a defined amount. Control factor F is the temperature of the washing solution for washing the sample after hybridization, and the units are degrees Celsius. Control factor G is the magnification of the salt concentration of the washing solution relative to a defined amount.

The inventors pretreated a negative sample under pretreatment conditions shown in Nos. 1 to 8 to prepare a sample, and measured the prepared sample to obtain first to third images. The inventors then calculated the ratio in each number of the number of cells in which the bright spots in the first image and the second image where any of the negative pattern and the positive patterns 1 to 3 changed by dividing the nucleus area of the image by the number of cells that could be extracted based on the third image, as shown in FIGS. 3A to 3D. That is, the inventors calculated the proportion of cells that can be analyzed among the detected cells. Hereinafter, the ratio of cells that can be analyzed among the detected cells is referred to as the "first index". As a result of verification by the inventors, in the case of number 5, the first index was 68%, which was the highest value compared with other pretreatment conditions.

The inventors determined that the pretreatment condition of number 5 is the condition that can perform the pretreatment most appropriately, and set a threshold value to determine whether pretreatment is appropriate based on the value of the first index at this time of 68%. Specifically, the inventors set the threshold value for determining that the pretreatment state is at the warning level to 50%, and set the threshold value for determining that the pretreatment state is at the abnormal level to 30%. Note that the threshold value of the warning level is set to a value smaller than the value of the first index acquired in the case where performing pretreatment is considered most appropriate, and the threshold value of the abnormality level may be set to a value less than the threshold value by a predetermined value.

In the pretreatment actually carried out by the inventors shown in FIG. 4, cells that can be analyzed are limited to cells of a negative pattern since a negative sample is used. However, when pretreatment is performed using an actual sample, most cells that can be analyzed become cells of either the negative pattern or the positive patterns 1 to 3. Therefore, as described above, the first index calculated by dividing the number of cells which conform to any of the negative pattern and positive patterns 1 to 3 by the number of cells from which the nuclear region can be extracted is not limited to a negative sample, and the first index also can be used as an index when pretreatment is appropriate for actual samples. Cells that can not be analyzed among the detected cells are those cells that did not correspond to any of the negative pattern and the positive patterns 1 to 3 because the pretreatment was not properly performed.

A procedure for actually determining whether pretreatment is appropriate using the first index is described below.

First, with a predetermined timing, for example, immediately before starting use of the fluorescence image analyzer 10 one day, the operator pretreats a negative sample which is a standard sample using the pretreatment part 20. The operator then sets the sample 20*a* prepared by pretreating the standard sample in the fluorescence image analyzer 10, and measures the sample 20*a*. The processing part 11 acquires the first to third images for each cell and extracts the region of the nucleus and the region of the bright spot.

The processing part 11 then acquires the number of cells that can be properly extracted from the nuclear region based on the third image as a first number, and acquires the number of cells in which bright spots in the first image and the second image match any of the negative pattern and positive patterns 1 to 3 as a second number. Then, the processing part 11 acquires the ratio of the second number to the first number as the first index. The processing part 11 compares the threshold values corresponding to the warning level and the abnormal level with the first index to determine whether pretreatment is appropriate. Specifically, when the first index is less than the warning level but equal to or more than the abnormal level, the processing part 11 determines that the pretreatment state is the warning level, and when the first index is less than the abnormal level, determines that the pretreatment state is the abnormal level.

As described above, the threshold value is set based on the first index at which pretreatment is considered to be most appropriate from the verification result, and the first index actually acquired based on the standard sample is compared with the set threshold value to determine whether the pretreatment is appropriate. In this way, when the pretreatment is not properly performed, the value of the actually acquired first index becomes smaller than the first index in the case where the pretreatment is appropriately performed. Therefore, it is possible to accurately determine whether pretreatment is appropriate by comparing the value of the actually acquired first index with the threshold value.

Note that the appropriateness of pretreatment can be determined even when using a sample 20*a* prepared by pretreating the actual sample collected from the subject, that is, the sample 20*a* prepared in the case of actually performing the analysis. The sample 20*a* based on the actual sample includes cells in which the bright spots in the first image and the second image are negative patterns shown in FIG. 3A, and cells in which the bright spots are positive pattern 1 shown in FIGS. 3B to 3D.

In this case, the processing part 11 also acquires the number of cells in which the bright spots in the first image and the second image match any of the negative pattern and the positive patterns 1 to 3 as the second number. The second number in this case is also the number of cells that can be analyzed among the detected cells. Therefore, also in this case, the processing part 11 divides the second number by the first number which is the detected cell number, so that the first index can be set as the same as in the case of the sample 20*a* based on the negative sample described above. The processing part 11 then compares the acquired first index with the threshold value of the warning level and the threshold value of the abnormality level similar to the case of the sample 20*a* based on the negative sample described above, and determines whether pretreatment is appropriate.

Second Index

As described above, when pretreatment is not properly performed, the target site may be insufficiently fluorescently labeled in some cases. The second index is an index focusing on the fact that the brightness of the bright spots in the first image and the second image decreases when the preprocessing is not properly performed. A procedure for actually determining whether pretreatment is appropriate using the second index is described below.

First, the operator pretreats a negative sample which is a standard sample by using the pretreatment part 20. The operator then sets the sample 20*a* prepared by pretreating the standard sample in the fluorescence image analyzer 10, and measures the sample 20*a*. The processing part 11 acquires the first to third images for each cell and extracts the region of the nucleus and the region of the bright spot.

Figure 5:
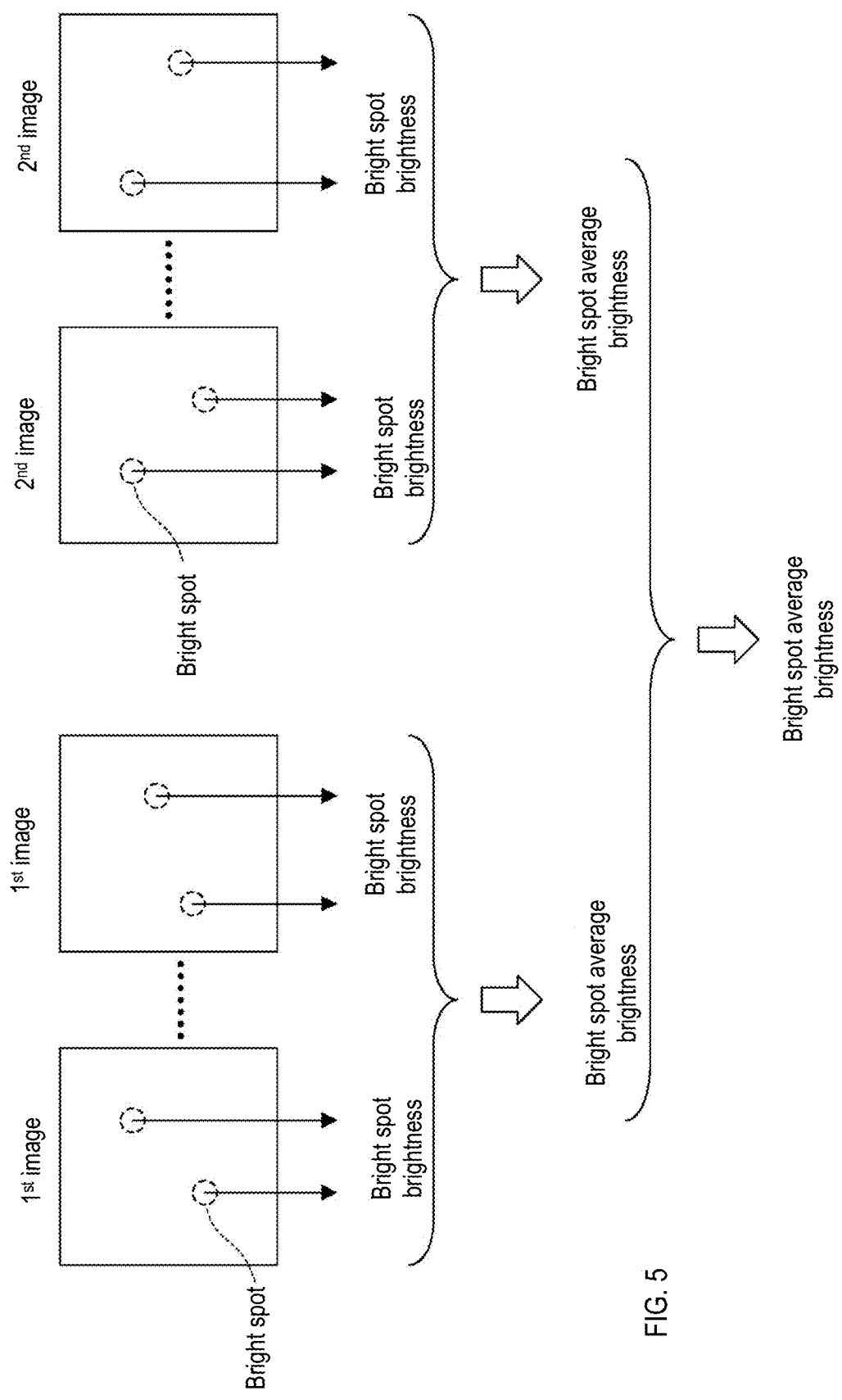
FIG. 5 illustrates a second index of the embodiment.

As shown in FIG. 5, the processing part 11 then acquires the brightness of the bright spots in the nucleus from the plurality of first images, and calculates the average brightness of the bright spots of the first image based on the acquired brightness of the bright spots. Similarly, the processing part 11 acquires the brightness of the bright spots in the nucleus from the plurality of second images, and calculates the average brightness of the bright spots of the second image based on the acquired brightness of the bright spots. The processing part 11 then calculates the average brightness of the bright points in all the cells based on the average brightness of the first image and the average brightness of the second image. Hereinafter, the average brightness of bright spots in all cells is referred to as the "second index".

The processing part 11 then compares the threshold value of the warning level and the threshold value of the abnormal level with the second index to determine whether pretreatment is appropriate. Specifically, when the second index is less than the warning level but equal to or more than the abnormal level, the processing part 11 determines that the pretreatment state is the warning level, and when the second index is less than the abnormal level, determines that the pretreatment state is the abnormal level.

Note that, in this case as well, the operator performs pretreatment of the negative sample under a plurality of pretreatment conditions in advance, and when the pretreatment is performed most appropriately, that is, the case where the value becomes the largest, acquires second index. The operator then presets the threshold of the warning level to a value that is smaller than the second index of the largest value by a predetermined value, and presets the threshold of the abnormal level to a value smaller than the value of the warning level.

Note that the second index also may be a value obtained by dividing the number of cells including a bright spot with brightness smaller than a predetermined value by the total number of cells. In this case, if pretreatment is not properly performed, the second index becomes large. Also in the case of using the second index, the appropriateness of pretreatment can be determined by using the sample 20*a* prepared by pretreating the actual sample collected from the subject similar to the first index.

Third Index

The third index is an index focusing on the fact that the brightness of the bright spots in the first image and the second image decreases and the S/N ratio based on the first image and the second image decreases when the pretreatment is not properly performed. A procedure for actually determining whether pretreatment is appropriate using the third index is described below.

First, the operator pretreats a negative sample which is a standard sample by using the pretreatment part 20. The operator then sets the sample 20a prepared by pretreating the standard sample in the fluorescence image analyzer 10, and measures the sample 20a. The processing part 11 acquires the first to third images for each cell and extracts the region of the nucleus and the region of the bright spot.

Figure 6:
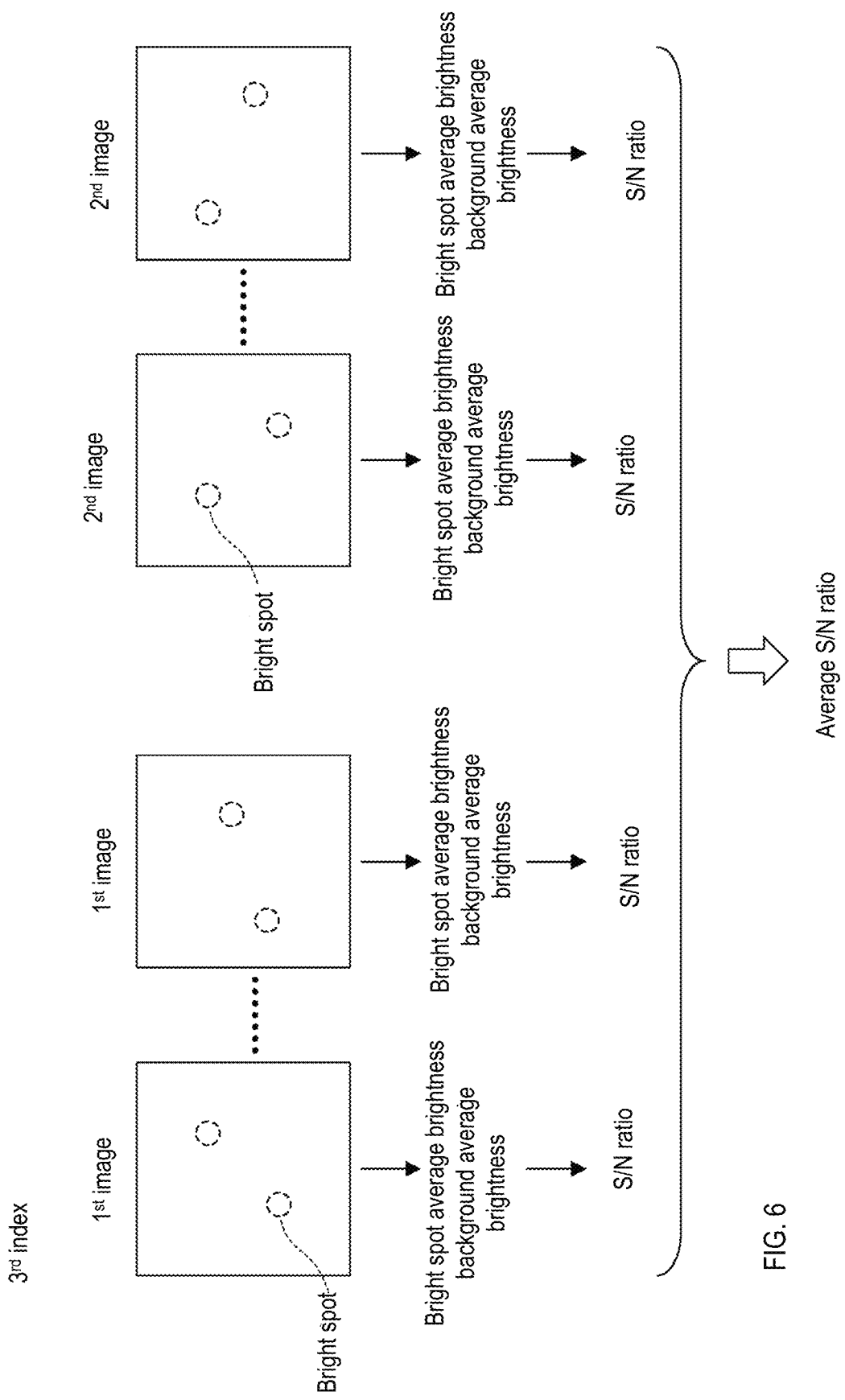
FIG. 6 illustrates a third index of the embodiment.

As shown in FIG. 6, the processing part 11 then calculates the average brightness of the bright spots in the nucleus from the plurality of first images and the average brightness of the area other than the bright spot area in the nucleus, that is, the background area of the bright spot. Similarly, the processing part 11 acquires the average brightness of the bright spots in the nucleus and the average brightness of the background area of the bright spots from the plurality of second images. The processing part 11 calculates the S/N ratio in each image by dividing the average brightness of bright spots by the average brightness of the background. The processing part 11 then averages the S/N ratios based on each image and calculates the average S/N ratio in all the cell. Hereinafter, the average S/N ratio in all cells is referred to as the "third index".

The processing part 11 then compares the threshold value of the warning level and the threshold value of the abnormal level with the third index to determine whether pretreatment is appropriate. Specifically, when the third index is less than the warning level but equal to or more than the abnormal level, the processing part 11 determines that the pretreatment state is the warning level, and when the third index is less than the abnormal level, determines that the pretreatment state is the abnormal level.

Note that, in this case as well, the operator performs pretreatment of the negative sample under a plurality of pretreatment conditions in advance, and when the pretreatment is performed most appropriately, that is, the case where the value becomes the largest, acquires S/N ratio. The operator then presets the threshold of the warning level to a value that is smaller than the third index of the largest value by a predetermined value, and presets the threshold of the abnormal level to a value smaller than the value of the warning level.

Figure 7:
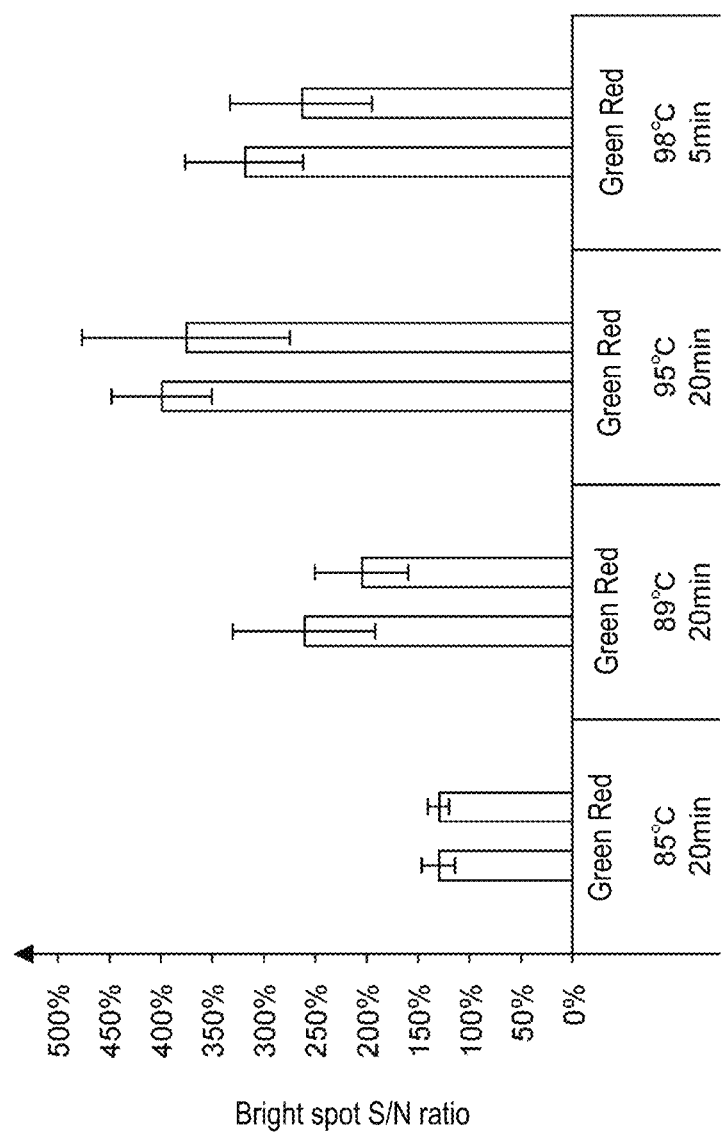
FIG. 7 illustrates a third index of the embodiment.

As shown in FIG. 7, the inventors calculated the average S/N ratio based on the first image including the green bright spot, and calculated the average S/N ratio based on the second image including the red bright spot by changing the heat denaturation temperature and the heat denaturation time in the pretreatment. In the example shown in FIG. 7, when the heat denaturation temperature is 95° C. and the thermal denaturation time is 20 minutes, both the average S/N ratio based on the first image and the average S/N ratio based on the second image became highest. Therefore, when the thermal denaturation temperature is 95° C. and the thermal denaturation time is 20 minutes, that is, when the most appropriate pretreatment is performed, the third index is approximately 385% since the average S/N ratio based on the first image is about 400% and the average S/N ratio based on the second image is about 370%. Therefore, according to the verification result shown in FIG. 7, 250% can be set as the threshold value representing the warning level, and 200% can be set as the threshold value representing the abnormal level.

Note that the third index also may be a value obtained by dividing the number of cells whose average S/N ratio is smaller than a predetermined value by the total number of cells. In this case, if pretreatment is not properly performed, the second index becomes large. Also in the case of using the third index, the appropriateness of pretreatment can be determined by using the sample 20a prepared by pre-treating the actual sample collected from the subject similar to the first index.

Fourth Index

When the pretreatment is properly performed, a bright spot is imaged as the state in which fluorescence is generated from one point of the target site, and the bright spot on the fluorescence image becomes a substantially circular shape. On the other hand, as described above, when pretreatment is not performed properly, nonspecific binding occurs and fluorescence may be generated from the peripheral portion of the target site. The fourth index is an index focusing on the fact that the circularity of the bright spots in the first image and the second image decreases when the preprocessing is not properly performed. A procedure for actually determining whether pretreatment is appropriate using the fourth index is described below.

First, the operator pretreats a negative sample which is a standard sample by using the pretreatment part 20. The operator then sets the sample 20a prepared by pretreating the standard sample in the fluorescence image analyzer 10, and measures the sample 20a. The processing part 11 acquires the first to third images for each cell and extracts the region of the nucleus and the region of the bright spot.

Figure 8:
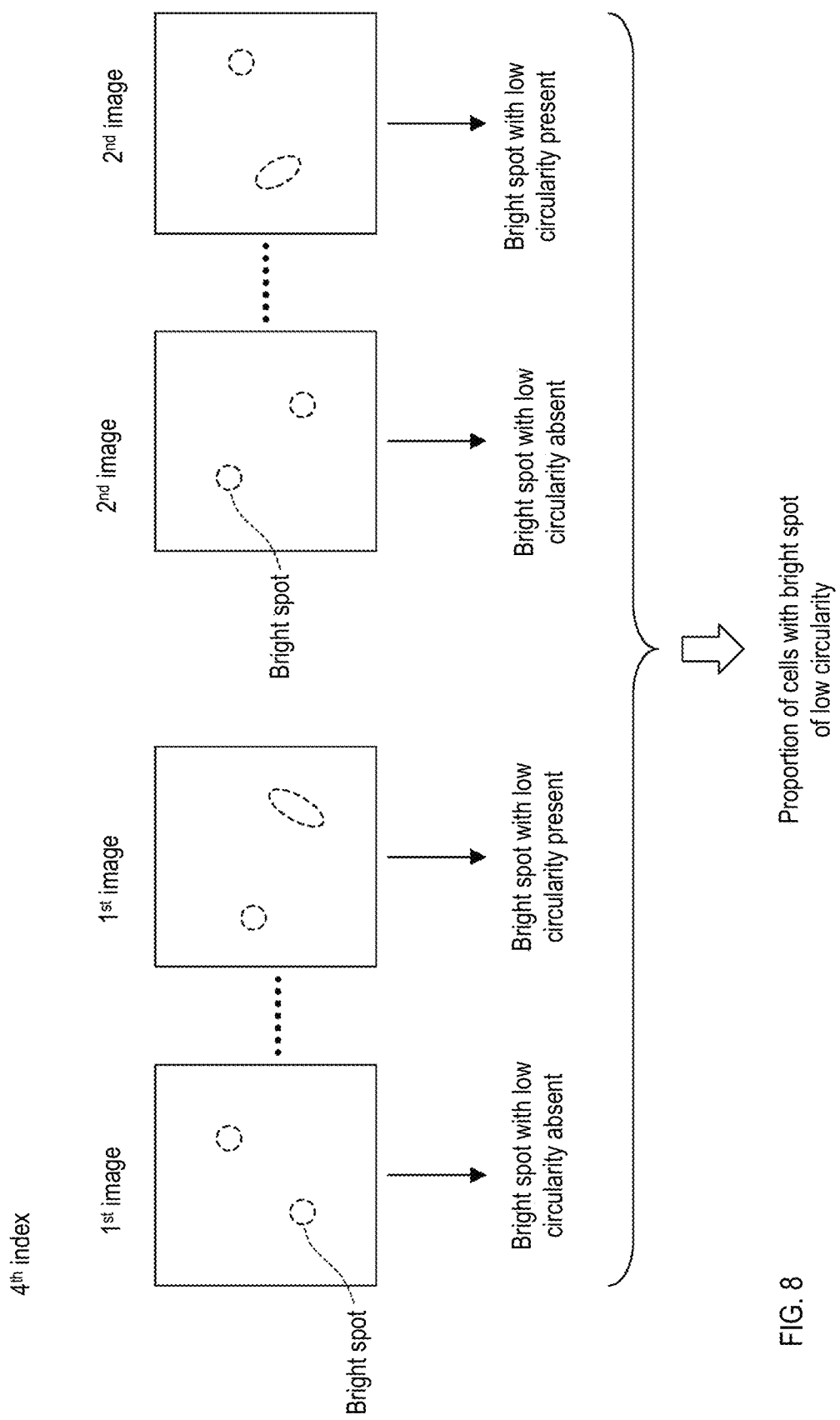
FIG. 8 illustrates a fourth index of the embodiment.

As shown in FIG. 8, the processing part 11 the calculates the circularity of each bright spot in the nucleus in the first image and the second image, and determines whether a predetermined number or more of bright spots whose circularity is lower than a predetermined value, that is, not circular, are present in each cell. In the example shown in FIG. 8, the processing part 11 determines whether there is one or more bright spot having a circularity lower than a predetermined value. The processing part 11 calculates the proportion of cells including a bright spot having a low circularity by dividing the number of cells including such a bright spot having the low circularity by the total number of cells. Hereinafter, the proportion of cells including bright spots with low circularity is referred to as the "fourth index".

The processing part 11 then compares the threshold value of the warning level and the threshold value of the abnormal level with the fourth index to determine whether pretreatment is appropriate. Specifically, when the fourth index is greater than the warning level but less than the abnormal level, the processing part 11 determines that the pretreatment state is the warning level, and when the fourth index is greater than the abnormal level, determines that the pretreatment state is the abnormal level.

Note that, in this case as well, the operator performs pretreatment of the negative sample under a plurality of pretreatment conditions in advance, and when the pretreatment is performed most appropriately, that is, the case where the value becomes the smallest, acquires fourth index. The operator then presets the threshold of the warning level to a value that is larger than the fourth index of the smallest value by a predetermined value, and presets the threshold of the abnormal level to a value larger than the value of the warning level by a predetermined value.

The fourth index also may be the average of the circularity of all the bright spots in all the cells. In this case, if pretreatment is not properly performed, the fourth index becomes small. Also in the case of using the fourth index, the appropriateness of pretreatment can be determined by using the sample 20a prepared by pre-treating the actual sample collected from the subject similar to the first index.

Fifth Index

As described above, when preprocessing is not performed properly, bright spots may become large due to nonspecific binding. The fifth index is an index focusing on the fact that the bright spots in the first image and the second image become larger when the preprocessing is not properly performed. A procedure for actually determining whether pretreatment is appropriate using the fifth index is described below.

First, the operator pretreats a negative sample which is a standard sample by using the pretreatment part 20. The operator then sets the sample 20*a* prepared by pretreating the standard sample in the fluorescence image analyzer 10, and measures the sample 20*a*. The processing part 11 acquires the first to third images for each cell and extracts the region of the nucleus and the region of the bright spot.

Figure 9:
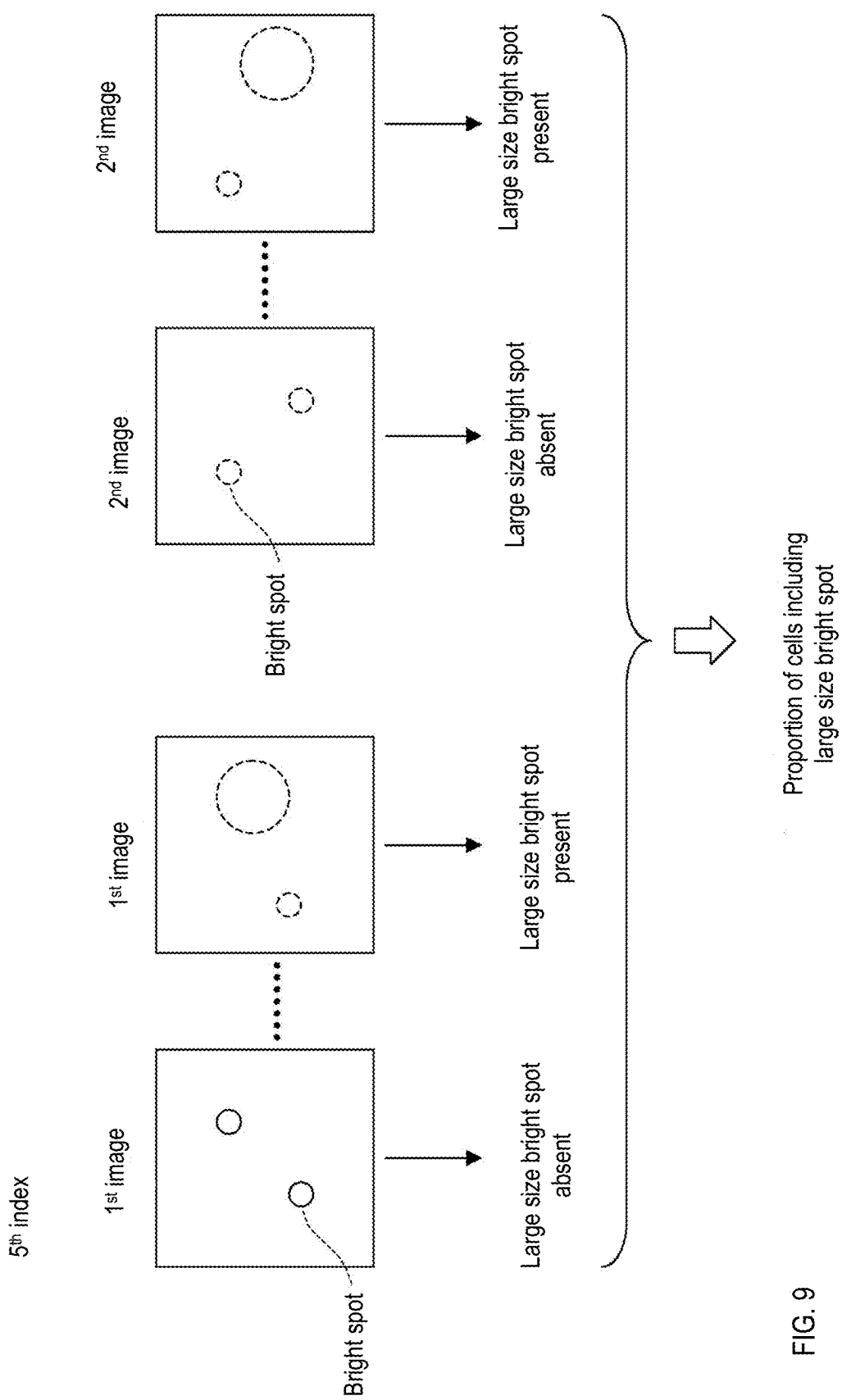
FIG. 9 illustrates a fifth index of the embodiment.

As shown in FIG. 9, the processing part 11 the calculates the size of each bright spot in the nucleus in the first image and the second image, and determines whether a predetermined number or more of bright spots whose size is larger than a predetermined value are present in each cell. In the example shown in FIG. 9, the processing part 11 determines whether there is one or more bright spot with a size larger than a predetermined value. Note that the size of the bright point is acquired by the area of the bright spot region in the bright spot image. The processing part 11 calculates the proportion of cells including large bright spots by dividing the number of cells including large bright spots by the total number of cells. Hereinafter, the proportion of cells including large bright spots is referred to as the "fifth index".

The processing part 11 then compares the threshold value of the warning level and the threshold value of the abnormal level with the fifth index to determine whether pretreatment is appropriate. Specifically, when the fifth index is greater than the warning level but less than the abnormal level, the processing part 11 determines that the pretreatment state is the warning level, and when the fifth index is greater than the abnormal level, determines that the pretreatment state is the abnormal level.

Note that, in this case as well, the operator performs pretreatment of the negative sample under a plurality of pretreatment conditions in advance, and when the pretreatment is performed most appropriately, that is, the case where the value becomes the smallest, acquires fifth index. The operator then presets the threshold of the warning level to a value that is larger than the fifth index of the smallest value by a predetermined value, and presets the threshold of the abnormal level to a value larger than the value of the warning level by a predetermined value.

Note that the fifth index also may be the average size of all the bright spots in all the cells. In this case, if pretreatment is not properly performed, the fifth index becomes large. Also in the case of using the fifth index, the appropriateness of pretreatment can be determined by using the sample 20*a* prepared by pre-treating the actual sample collected from the subject similar to the first index.

Sixth Index

As described above, when pretreatment is not properly performed, the target site may be insufficiently fluorescently labeled in some cases. The sixth index is an index focusing on the fact that the number of the bright spots in the first image and the second image decreases when the preprocessing is not properly performed.

First, the operator pretreats a negative sample which is a standard sample by using the pretreatment part 20. The operator then sets the sample 20*a* prepared by pretreating the standard sample in the fluorescence image analyzer 10, and measures the sample 20*a*. The processing part 11 acquires the first to third images for each cell and extracts the region of the nucleus and the region of the bright spot.

Figure 10:
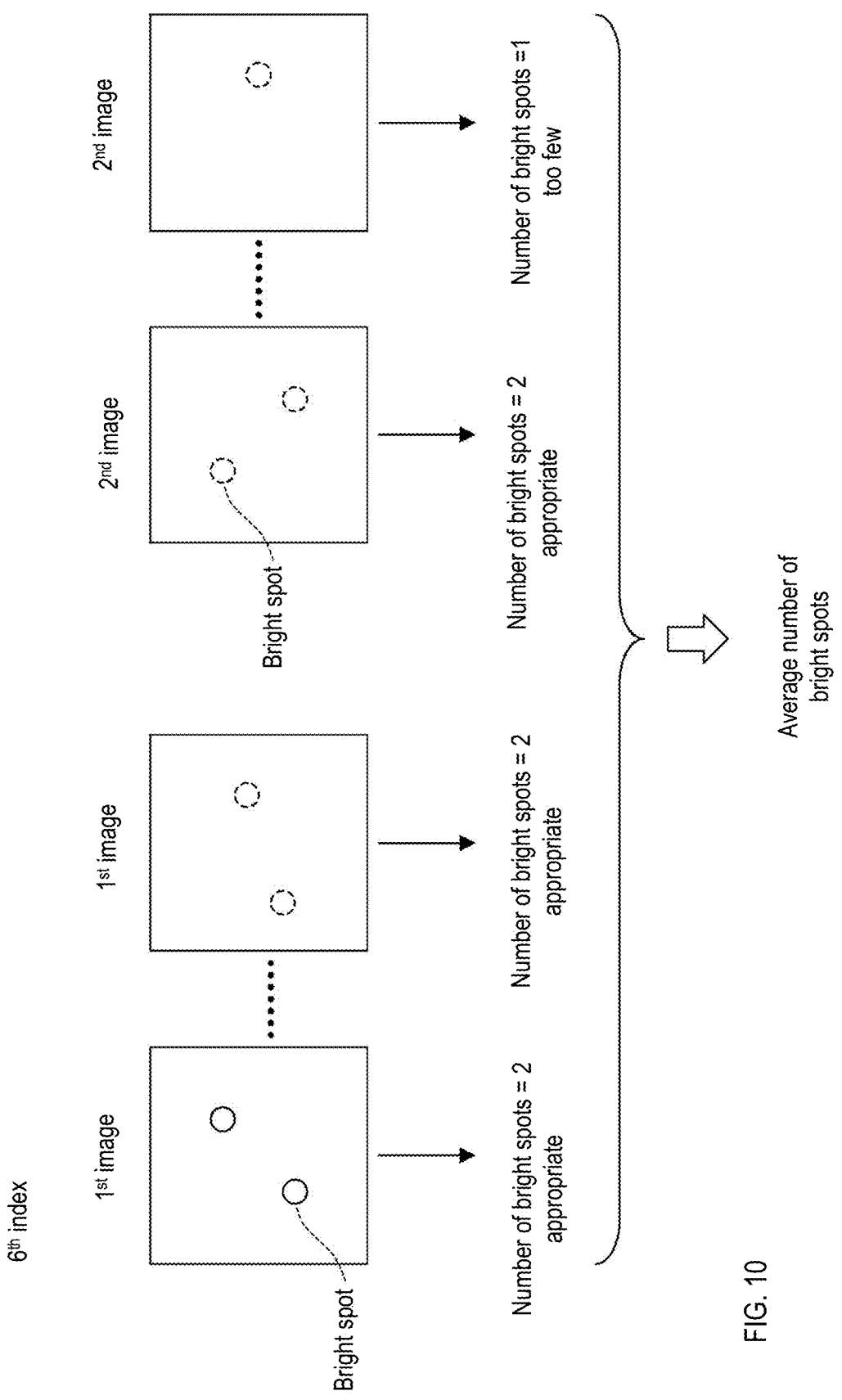
FIG. 10 illustrates a sixth index of the embodiment.

As shown in FIG. 10, the processing unit 11 then calculates the number of bright spots in the nucleus in the first image and the second image. Then, the processing part 11 averages the number of bright spots based on each image, and calculates the average value of the bright spots in all the cells. Hereinafter, the average value of the number of bright spots in all cells is referred to as the "sixth index".

The processing part 11 then compares the threshold value of the warning level and the threshold value of the abnormal level with the sixth index to determine whether pretreatment is appropriate. Specifically, when the sixth index is less than the warning level but equal to or more than the abnormal level, the processing part 11 determines that the pretreatment state is the warning level, and when the sixth index is less than the abnormal level, determines that the pretreatment state is the abnormal level. Note that in this case, if pretreatment is not properly performed, the value of the sixth index becomes 2. The operator then presets the threshold of the warning level to a value that is smaller than 2 by a predetermined value, and presets the threshold of the abnormal level to a value smaller than the value of the warning level.

Note that the sixth index may be the degree of divergence from 2 which is the ideal value when the pretreatment is appropriately performed. In this case, if pretreatment is not properly performed, the sixth index becomes large. The sixth index may be a value obtained by dividing the number of cells with fewer than two bright spots by the total number of cells. In this case, if pretreatment is not properly performed, the sixth index becomes large.

Also in the case of using the sixth index, the appropriateness of pretreatment can be determined by using the sample 20*a* prepared by pre-treating the actual sample collected from the subject similar to the first index. In this case, since positive cells may be mixed in the sample, the ideal value of the sixth index when the pretreatment is properly performed is slightly larger than 2. However, in consideration of the probability that a positive cell actually exists, it is possible to use a threshold value of the warning level and a threshold value of the abnormal level similar to those based on a negative cell as described above.

Note that although the first to sixth indices are calculated based on both the first image and the second image, the indices also may be calculated from either one of the fluorescence images.

Embodiments 1 to 7 in which pretreatment appropriateness is determined using the first to sixth indices, and abnormal cells are detected by analyzing a sample are described below. The fluorescence image analyzer 10 and the pretreatment part 20 shown in FIG. 1 are used in embodiments 1 to 7, unless otherwise mentioned.

First Embodiment

As shown in FIG. 11A, in step S11, the pretreatment part 20 pre-treats a negative sample as a standard sample to prepare a sample 20*a*. Step S11 includes a step of hybridizing a nucleic acid probe labeled with the fluorescent dye and the BCR region and the ABL region in the nucleic acid of the negative sample. In step S12, the processing part 11 measures the sample 20*a* prepared in the pretreatment in step S11. Specifically, the processing part 11 causes the sample 20*a* prepared from a negative sample to flow through the flow path 111 of the flow cell 110, irradiates the flow path 111 with light from the light sources 121 to 124, and captures the fluorescence generated from the sample 20*a* and the light transmitted through the sample 20*a* via the imaging part 154 to acquire the first to third images and a bright field image. The processing part 11 stores the first to third images and the bright field image in the memory part 12.

In step S13, the processing part 11 acquires the first to sixth indices and the determination result of whether pretreatment is appropriate is acquired as information based on the index. Specifically, the processing part 11 extracts the region of the nucleus and the region of the bright spot based on the first to third images. As described above, the processing part 11 then calculates the first to sixth indices, and determines whether pretreatment is appropriate based on the calculated first to sixth indices. The warning level threshold value and the abnormal level threshold value used for the determination based on the first to sixth indices are stored in the memory part 12. The processing part 11 stores the values of the first to sixth indices and the determination results based on the first to sixth indicators in the memory part 12. In step S14, the processing part 11 displays information based on the index on the display part 13. Specifically, the processing part 11 displays on the display part 13 a screen 210 including the determination result and the first to sixth indices acquired in step S13.

As shown in FIG. 11B, the screen 210 displays the values of the first to sixth indices and the determination results based on the first to sixth indices, respectively. When the screen 210 is configured in this way, the operator can determine whether pretreatment has been appropriately performed based on each index. If the operator determines that the pretreatment was inappropriate, the operator can take measures such as reviewing each process included in the pretreatment and performing pretreatment again. When the operator determines that the pretreatment is appropriate, the operator analyzes the actual sample collected from the subject, as shown in FIG. 12A.

Figure 12B:
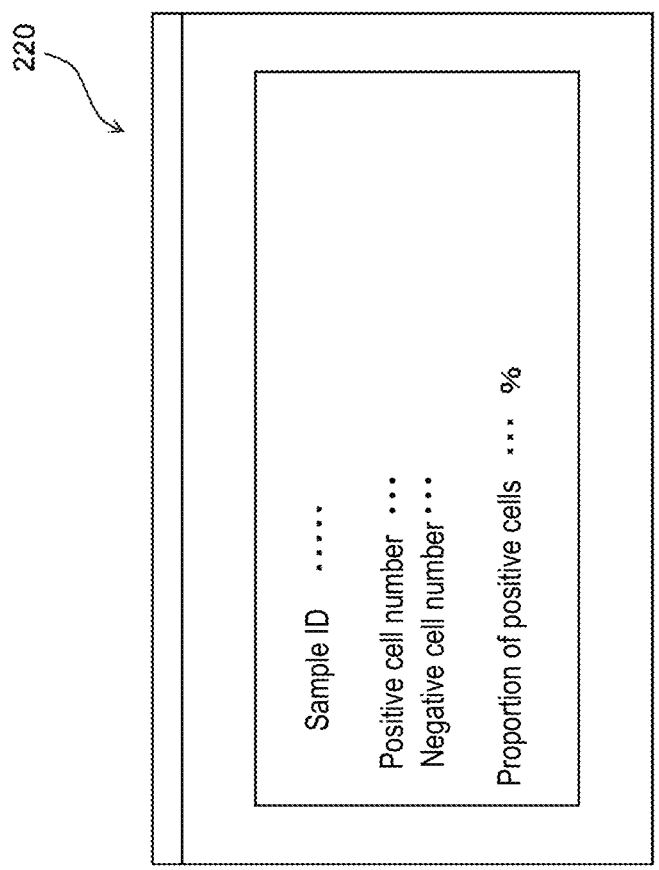
FIG. 12B schematically shows the structure of a screen displayed on the display part of the first embodiment.
Figure 12A:
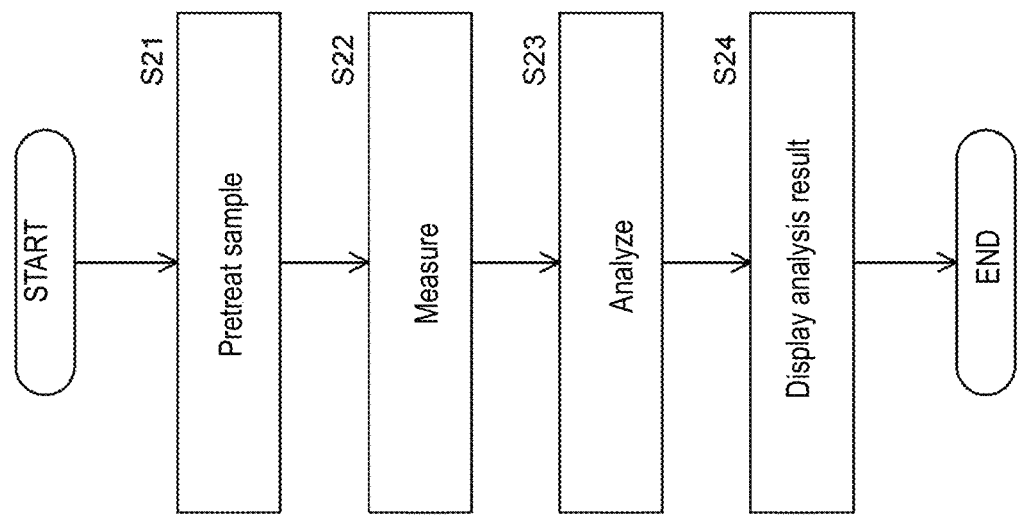
FIG. 12A is a flow chart showing the process of displaying the analysis results of the first embodiment.

As shown in FIG. 12A, in step S21, the pretreatment part 20 performs pretreatment on the sample collected from subject and that has been subjected to processing such as centrifugation to prepare sample 20a, as in step S11 of FIG. 11A. In step S22, the processing part 11 measures the sample 20a prepared by the pretreatment of step S21 in the same manner as in step S12 of FIG. 11A.

In step S23, the processing part 11 performs analysis. Specifically, based on the first to third images, the processing part 11 counts the cells whose bright spots are negative patterns shown in FIG. 3A, that is, negative cells. The processing part 11 also counts the cells in which the bright spots are any of the positive patterns 1 to 3 shown in FIGS. 3B to 3D, that is, positive cells, based on the first to third images. The processing part 11 also calculates the ratio of positive cells to all cells by dividing the number of positive cells by the total number of cells. In step S24, the processing part 11 displays the screen 220 including the analysis result acquired in step S23 on the display unit 13.

As shown in FIG. 12B, the screen 220 displays the sample ID for identifying the sample, the number of positive cells, the number of negative cells, and the ratio of positive cells to all cells. When the screen 220 is configured as described above, the physician or the like can use the display content of the screen 220 for determining whether the sample is positive or negative. Note that when the proportion of positive cells exceeds a predetermined threshold value, the processing part 11 also may display, for example, "Potentially Positive?" to suggest the sample is positive.

Note that in step S13 the processing part 11 calculates the first to sixth indices without performing the determination regarding the appropriateness of the pretreatment, and displays the screen 210 including only the values of the first to the sixth indices on the display part 13 in step S14. In this case, for example, the operator checks the values of the first to sixth indices and determines whether the pretreatment is appropriate.

Second Embodiment

In the second embodiment, pretreatment is performed on the actual sample collected from the subject, and the appropriateness of the pretreatment is determined based on the sample 20a prepared from the actual pretreated sample.

As shown in FIG. 13A, in step S31, the pretreatment part 20 performs a process on the sample collected from the subject and that has been subjected to a process such as centrifugation to prepare sample 20a, as in step S21 of FIG. 12A. In step S32, the processing part 11 measures the sample 20a prepared by the pretreatment of step S31 in the same manner as in step S12 of FIG. 11A.

In step S33, the processing part 11 acquires information based on the index in the same manner as in step S13 of FIG. 11A, and performs analysis similarly to step S23 of FIG. 12A.) In step S34, the processing part 11 displays the information based on the index on the display part 13 in the same manner as in step S14 of FIG. 11A, and outputs the analysis result to the display part 13 as in step S24 of FIG. 12A. Specifically, in step S34, the processing part 11 displays the screen 230 including the index, the determination result, and the analysis result on the display part 13.

As shown in FIG. 13B, the screen 230 displays the values of the first to sixth indices, the determination results based on the first to sixth indices, the sample ID for identifying the sample, the number of positive cells, the number of negative cells, and the proportion of positive cells to all cells. When the screen 230 is configured in this manner, the physician or the like can determine whether the sample is positive or negative while checking appropriateness of pretreatment of the sample. For example, when the determination result of the pretreatment is appropriate, the physician or the like determines that the reliability of the analysis result is high and can diagnose the sample with high accuracy. On the other hand, if the determination result of the pretreatment is inappropriate, the physician or the like can determine that the reliability of the analysis result is low and take measures such as suspending the diagnosis of the sample. In addition, it is not necessary to use a standard sample for determining pretreatment appropriateness.

Note that in step S33 the processing part 11 calculates the first to sixth indices without performing the determination regarding the appropriateness of the pretreatment, and displays the screen 230 including the values of the first to the sixth indices and the analysis results on the display part 13 in step S34.

Third Embodiment

In the third embodiment, similarly to the second embodiment, pretreatment is performed on the actual sample collected from the subject to determine whether pretreatment is appropriate. In the third embodiment, first to sixth indicators in a predetermined period are calculated, and pretreatment appropriateness is determined.

Every time pretreatment is performed, the processing part 11 stores the date and time when the pretreatment was performed, the sample ID, the first to third images, and the bright field image as information related to the bright spot in the database 12a. Database 12a is stored in the memory part 12. Note that the processing part 11 extracts the region of the bright spot, the brightness of the bright spot, and the background region from the first to the third images, and stores the extracted information as information related to the bright spot in the database 12a.

Every time pretreatment is performed, the processing part 11 acquires the first to sixth indices based on the first to third images, displays the acquired first to sixth indices as shown in FIG. 14B, and stores the indices in the database 12b. That is, the processing part 11 acquires the first to sixth indices for each sample 20 prepared by pretreatment, and stores the obtained first to sixth indices in the database 12b in association with the sample 20a. Database 12b is stored in the memory part 12. The processing part 11 also may store the determination results based on the first to sixth indices in the database 12b. When the first to sixth indices are stored for each sample 20a in this manner, the processing part 11 can smoothly display the first to sixth indices on the display part 13 for the pretreatments performed in the past. Note that the processing part 11 also may store the first to sixth indices in the database 12b with a predetermined timing, for example, with the timing when the analyses of one day is completed.

Figure 15A:
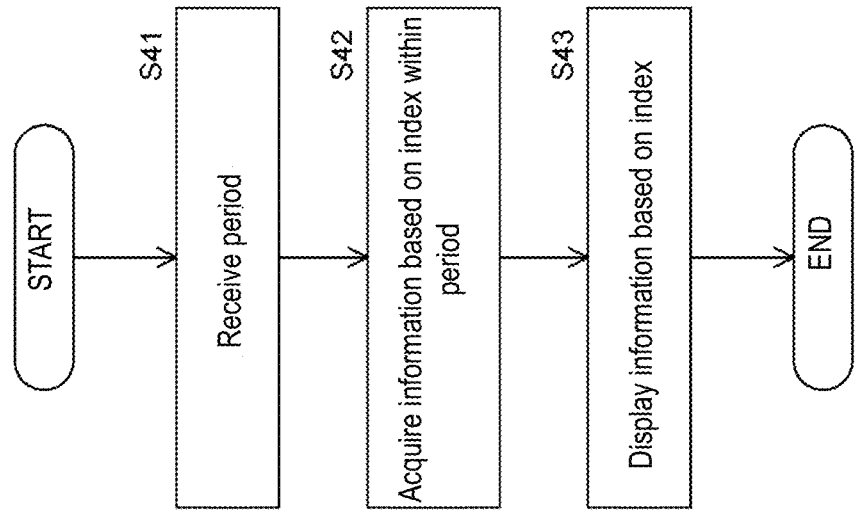
FIG. 15A is a flow chart showing the process of displaying the determination results of whether pretreatment is appropriate according to the third embodiment.

As shown in FIG. 15A, in step S41, the processing part 11 receives the period input by the operator via the input part 14. The period consists of the start date and time and the end date and time.

In step S42, the processing part 11 acquires information based on the index within the period based on the first to third images included in the period received in step S41 from the database 12a shown in FIG. 14A. Specifically, the processing part 11 calculates first to sixth indices in the same manner as described above based on all the first to third images included in the reception period, and determines whether pretreatment is appropriate as described above based on the calculated first to sixth indices. Note that the processing part 11 also may acquire the first to sixth indices of the reception period by averaging the same indices included in the reception period based on the database 12b shown in FIG. 14B. Good In step S43, the processing part 11 displays on the display part 13 a screen 240 including information based on the indices acquired in step S42, that is, a screen 240 including first to sixth indices, and the determination results of whether pretreatment is appropriate.

Figure 15B:
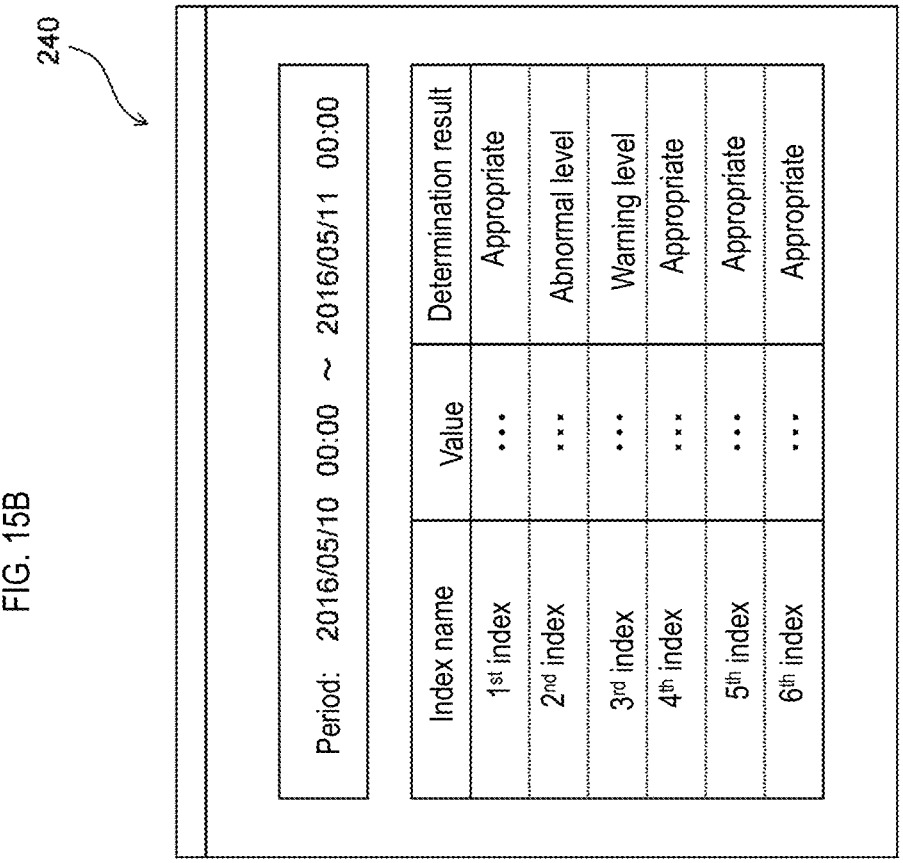
FIG. 15B schematically shows the structure of a screen displayed on the display part of the third embodiment.

As shown in FIG. 15B, the screen 240 displays the period input by the operator, the first to sixth indices of the reception period, and the determination results based on the first to sixth indices. When the screen 240 is configured in this manner, the operator can know the first to sixth indices and the determination result of the pretreatment appropriateness in a predetermined time span. In the example shown in FIG. 15B, the operator can know the index and the judgment result on the day of "2016 May 10".

Note that in step S42 the processing part 11 calculates the first to sixth indices without performing the determination regarding the appropriateness of the pretreatment, and displays the screen 240 including only the values of the first to the sixth indices on the display part 13 in step S43. In step S41, although the processing part 11 also acquires and displays information based on the index based on the period input by the operator, the processing part 11 also may automatically set the time 0 to 24 as one day in accordance with to the operator's start instruction.

Fourth Embodiment

In the fourth embodiment, the time course of the index is graphically displayed additionally in the third embodiment.

As shown in FIG. 16A, in step S51, the processing part 11 receives the period, display unit, and selected index input by the operator via the input part 14. As in the third embodiment, the period includes the start date and time and the end date and time. The display unit is the time span of one day, one hour, and the like. The selected index is one of the first to sixth indices.

In step S52, the processing part 11 acquires information based on the selected index of each display unit based on all the first to third images included in the period received in step S51 from the database 12a shown in FIG. 14A. For example, when the display unit is one day and the selected index is the first index, the processing part 11 acquires the first index of each day and the pretreatment determination result based on the first index within the period. Note that the processing part 11 also may acquire information based on the selected index for each display unit within the period based on the database 12b shown in FIG. 14B. In step S53, the processing part 11 displays the screen 250 including the graph based on information acquired in step S52 on the display unit 13.

As shown in FIG. 16B, the screen 250 displays an area for displaying the period, display unit, and selected index input by the operator, and a graph based on the information acquired in step S52. In the example shown in FIG. 16B, the temporal transition of the first index each day for 10 days is shown on the graph, and the graph shows the warning level and the abnormal level together. When the screen 250 is configured in this manner, the operator can visually comprehend the temporal transition of the first to sixth indices within a predetermined period, so that the state of the pretreatment can be more accurately grasped.

Note that although the processing part 11 creates a graph based on the information input by the operator in step S51, the processing part 11 also may automatically set the display unit as one day and set the period as 10 days from the current day. The processing part 11 also may display six graphs based on the first to sixth indices on the screen 250 without receiving a selected index. The processing part 11 also may display the value of the index at each point in the graph.

Fifth Embodiment

In the fifth embodiment, instead of the screen 210 of the first embodiment shown in FIG. 11B, the screen 260 shown in FIG. 17 is displayed on the display part 13. As shown in FIG. 17, the screen 260 displays, in addition to the first to sixth indices and the determination result, a radar chart visually showing the correlation between the first to the sixth indices. Note that in this case each index is calculated so that plotted points move outward as the values of the first to sixth indices increase. For example, although the fourth index is the proportion of cells including bright spots with low circularity, the fourth index in this case is the proportion of cells that do not contain bright spots with low circularity.

When the screen 260 is configured in this way, the operator can visually grasp the correlation between the first to the sixth indices. Note that the radar chart shown in FIG. 17 also may be displayed in the screen 230 of the second embodiment shown in FIG. 13B.

Sixth Embodiment

As shown in FIG. 18, the fluorescence image analyzer 10 of the sixth embodiment includes an imaging unit 300 including a fluorescence microscope in place of the imaging unit 100 shown in FIG. 1. In other respects the configuration of the sixth embodiment is the same as the configuration shown in FIG. 1.

The imaging unit 300 includes light sources 301 to 303, a mirror 304, dichroic mirrors 305 and 306, a shutter 311, a quarter-wave plate 312, a beam expander 313, a condenser lens 314, a dichroic mirror 315, an objective lens 316, a stage 320, a condenser lens 331, an imaging part 332, and controllers 341 and 342. A slide glass 321 is placed on the stage 320. The sample 20a prepared by the pretreatment via the pretreatment part 20 is placed on the slide glass 321.

The light sources 301 to 303 are respectively identical to the light sources 121 to 123 shown in FIG. 1. The mirror 304 reflects the light from the light source 301. The dichroic mirror 305 transmits the light from the light source 301 and reflects the light from the light source 302. The dichroic mirror 306 transmits the light from the light sources 301 and 302, and reflects the light from the light source 303. The optical axes of the light from the light sources 301 to 303 are made to coincide with each other by the mirror 304 and the dichroic mirrors 305 and 306.

The shutter 311 is driven by the controller 341 to switch between a state of passing light emitted from the light sources 301 to 303 and a state of blocking light emitted from the light sources 301 to 303. In this way the irradiation time of light to the sample 20a is adjusted. The quarter-wavelength plate 312 converts the linearly polarized light emitted from the light sources 301 to 303 into circularly polarized light. Fluorescent dye bound to the nucleic acid probe reacts to light of a predetermined polarization direction. Therefore, by converting the excitation light emitted from the light sources 301 to 303 into circularly polarized light, the polarization direction of the excitation light easily coincides with the polarization direction in which the fluorescent dye reacts. In this way it is possible to efficiently excite the fluorescent dye to fluorescence. The beam expander 313 broadens the irradiation region of the light on the slide glass 321. The condenser lens 314 condenses the light from the objective lens 316 so as to irradiate parallel rays on the slide glass 321.

The dichroic mirror 315 reflects light emitted from the light sources 301 to 303, and transmits fluorescent light given off from the sample 20a. The objective lens 316 directs the light reflected by the dichroic mirror 315 to the slide glass 321. The stage 320 is driven by the controller 342. Fluorescent light given off from the sample 20a passes through the objective lens 316 and passes through the dichroic mirror 315. The condenser lens 331 collects the fluorescent light transmitted through the dichroic mirror 315 and directs the light to the imaging surface 332a of the imaging part 332. The imaging part 332 captures an image of the fluorescent light irradiated on the imaging surface 332a to generate a fluorescence image. The imaging part 332 is configured, for example, by a CCD or the like.

The controllers 341 and 342 and the imaging part 332 are connected to the processing part 11 shown in FIG. 1, and the processing part 11 controls the controllers 341 and 342 and the imaging part 332, and receives the fluorescence image captured by the imaging part 332. As shown in FIG. 1, the fluorescent image captured by the imaging part 332 may be in a state of close contact with the cell as shown in FIG. 2A unlike the case where the flow cell 110 is used. Therefore, the processing part 11 performs a process of dividing the obtained fluorescence image for each nucleus of a cell, or a process of setting a region corresponding to one nucleus of a cell in the fluorescence image or the like.

In the sixth embodiment as in the other embodiments, the first to the sixth indices are acquired based on the first to third images since the first to third images can be acquired, and it is possible to determine whether pretreatment is appropriate based on the acquired first to sixth indices.

Seventh Embodiment

Figure 19:
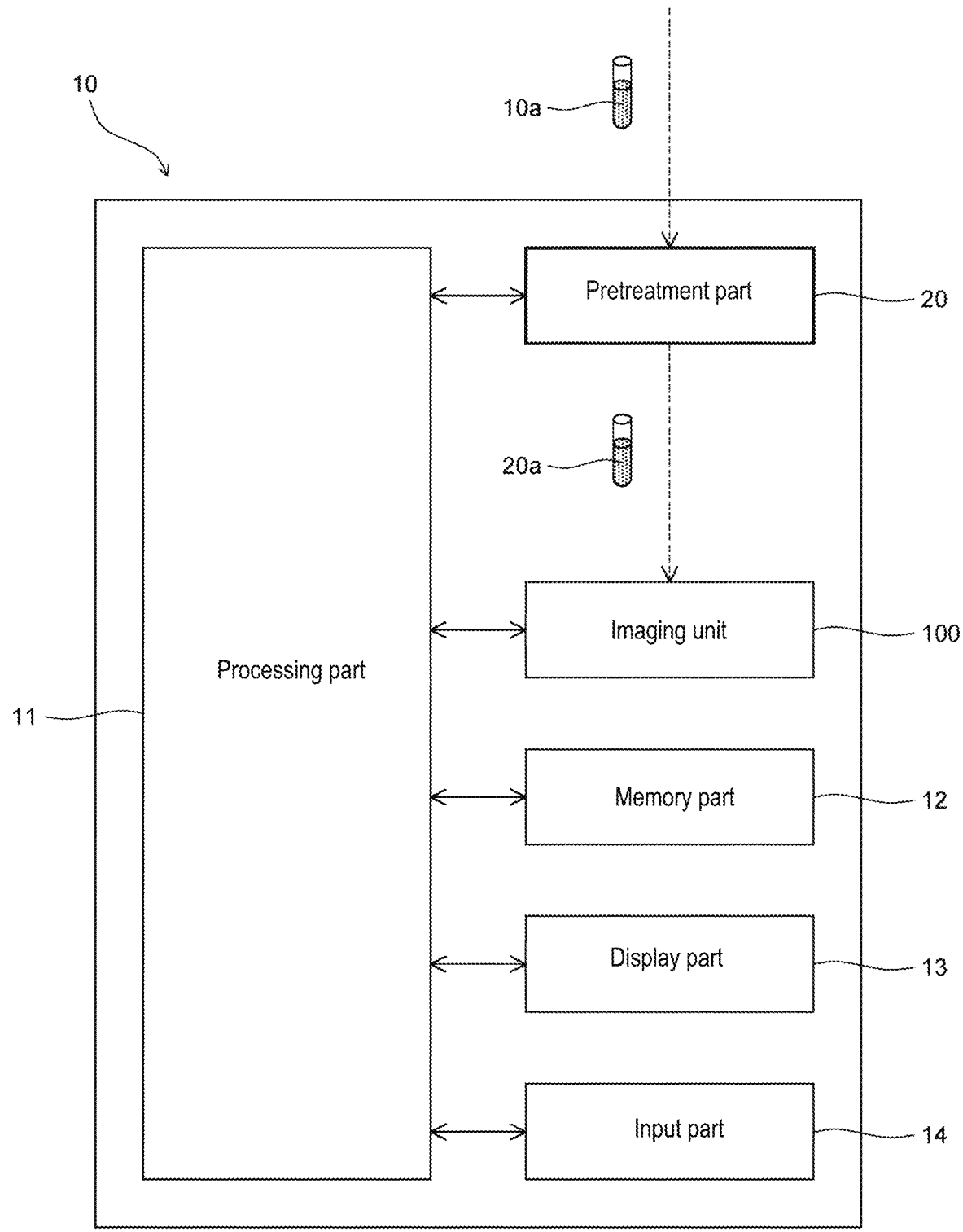
FIG. 19 schematically shows the structure of the fluorescence image analyzer of a seventh embodiment.

As shown in FIG. 19, the fluorescence image analyzer 10 of the seventh embodiment includes the pretreatment part 20 shown in FIG. 1. The processing part 11 is connected to the pretreatment part 20, receives signals from the pretreatment part 20, and controls the pretreatment part 20. When the pretreatment part 20 receives the sample 10a collected from a subject and that has been processed by centrifugation or the like, the pretreatment part 20 performs pretreatment on the sample 10a to prepare the sample 20a. The imaging unit 100 measures the sample 20a prepared by the pretreatment part 20, and acquires the first to third fluorescence images and the bright field image. In other respects the configuration of the seventh embodiment is the same as the configuration shown in FIG. 1.

When the fluorescence image analyzer 10 includes the pretreatment part 20 as described above, the operator automatically performs the pretreatment merely by setting the sample 10a in the fluorescence image analyzer 10, and the sample 20a is prepared by the pretreatment is automatically analyzed. The processing part 11 also acquires the first to sixth indices, and determines whether pretreatment by the pretreatment part 20 is appropriate. In this way the operator can grasp whether the pretreatment was appropriate in the analysis of the sample automatically performed by the fluorescence image analyzer 10.

Eighth Embodiment

As shown in FIG. 20, the memory part 12 of the eighth embodiment stores bright spot patterns for determining whether a cell is positive or negative. The bright spot pattern of FIG. 20A shows the state of bright spots in the fluorescence image exemplified in FIGS. 3A to 3D. In the pattern of the bright spot shown in FIG. 20A, "G" represents the green bright spot in the first image, "R" represents the red bright spot in the second image, "F" represents the fusion bright spot, that is, a yellow bright spot in the composite image. The numbers immediately following G, R, F indicate the number of bright spots of G, R, and F, respectively. For example, in the case of "G 2 R 2 F 0", the number of green bright spots in the first image is two, the number of red bright spots in the second image is two, and the number of yellow bright spots in the composite image is zero respectively.

Note that G also may represent the green bright spot of the composite image and R may represent the red bright spot in the composite image. In this case, the patterns of the bright spots shown in the 1st to 4th rows in FIG. 20A are "G 2 R 2 F 0", "G 1 R 2 F 1", "G 1 R 1 F 2", and "G 1 R 1 F 1".

The patterns of the bright spots shown in the first to fourth rows of FIG. 20A correspond to the bright spots of the fluorescence images shown in FIGS. 3A to 3D, respectively. The pattern based on the bright spot shown in FIG. 20A is associated with a determination based on the pattern of the bright spot. For example, "negative" is associated with the pattern of the bright spot in the first row, and "positive" is associated with the pattern of the bright spot in the second row. Note that the memory part 12 stores not only the patterns of the four bright spots shown in FIG. 20A but also a plurality of possible combinations thereof.

In the eighth embodiment, the same processing is performed as that of the first embodiment shown in FIG. 12A. A process different from that of the first embodiment will be described below.

In step S23, the processing part 11 extracts bright points from the fluorescence image for each of the plurality of cells included in the sample 20a in the same manner as the procedure described with reference to FIGS. 2A to 2D. Then, the processing part 11 classifies each of the plurality of cells based on the pattern of the bright spots, and the processing part 11 generates information used for determining whether the sample 20a is positive or negative based on the classification results of the plurality of cells.

Specifically, in step S23, the processing part 11 compares the pattern of the bright spot of the cell with the patterns of the bright spot stored in the memory part 12 shown in FIG. 20A, and determines whether the cell is positive or negative for each cell of the plurality of cells. When the bright spot pattern of the cell matches the positive pattern, the processing part 11 determines that the cell is positive, and when the bright spot pattern of the cell matches the negative pattern, the processing part 11 determines that the cell is negative. The processing part 11 then generates the number of positive cells, the number of negative cells, the ratio of the number of positive cells to the number of detected cells, the ratio of the number of negative cells to the number of detected cells, information on a pattern determined based on the number and color of bright spots, and information suggesting whether the sample 20a is positive or negative. The information generated in step S23 will be described later with reference to FIG. 20B.

In step S24, the processing part 11 displays the screen 221 including the information generated in step S23 on the display part 13. As shown in FIG. 20B, the display content on the screen 221 is invariably information used for determining whether the sample 20a is positive or negative.

As shown in FIG. 20B, the information related to the pattern determined on the basis of the number and the color of the bright spots includes the pattern of the bright spot shown in FIG. 20A, the number of cells matching this bright spot pattern, and the proportion of cells matching the bright spot pattern relative to the total number of cells. In this way the information related to the pattern determined based on the number and the color of the bright spots includes the result of classifying each of the plurality of cells based on the pattern of the bright spots.

In the case where the screen 221 shown in FIG. 20B is displayed, the pattern of the bright spot considered as positive is selected in advance from the positive bright spot pattern shown in FIG. 20A. Then, the cells that match the selected positive bright spot pattern are determined to be positive. The number of positive cells displayed on the screen 221 is the number of cells matching the selected positive bright spot pattern. Therefore, assuming that the number of negative cells is N1 and the number of positive cells in this case is N2, the proportion of positive cells is obtained by dividing N2 by N1+N2, and the proportion of negative cells is obtained by dividing N1 by N1+N2.

Information indicating whether the sample 20a is positive or negative is composed of character information such as "potentially positive?" or "potentially negative?" and the like. For example, when the proportion of positive cells is larger than a predetermined threshold value or the ratio of negative cells is smaller than a predetermined threshold value, "potentially positive?" is displayed. When the proportion of negative cells is larger than a predetermined threshold value or the proportion of positive cells is smaller than a predetermined threshold value, "potentially negative?" is displayed. The display may not be performed instead of "potentially negative?". Information based on the index also may be displayed together in screen 221 similarly to FIG. 13B.

According to the eighth embodiment, the physician or the like can refer to the display contents of the screen 221, and can highly accurately determine whether the sample 20a and sample that is the basis of sample 20a is positive or negative.

Other Embodiments

In the above-described embodiments, the target site is the BCR gene and the ABL gene, but the present invention is not limited to this configuration inasmuch as other target gene regions may also be used. In the case of chronic myelogenous leukemia, translocation may occur in the BCR gene and the ABL gene, but abnormality similarly may be found in specific gene regions even in specific diseases. In the case where the target site is another gene region, the processing part 11 calculates the proportion of the number of positive cells related to a specific disease or the number of positive cells to the number of detected cells, and displays the calculated number or proportion on the display part 13 as the analysis result. Also in this case, as in the eighth embodiment, the processing part 11 generates information used for determining whether the sample 20a is positive or negative as shown in FIG. 20B, and displays the generated information on the display part 13.

The target site may be, for example, the HER2 gene and CEP17, which is a centromere region of chromosome 17. The HER2 gene is amplified in association with cell carcinogenesis, and CEP17 does not amplify in conjunction with cell carcinogenesis. Therefore, when the HER2 gene and CEP17 are used as the target site, it is possible to determine the appropriateness of pretreatment on the basis of the sample 20a prepared by pretreating the negative sample. That is, in the case of a negative sample, it is possible to determine the appropriateness of the pretreatment based on the fact that there are two bright spots of the HER2 gene and two bright spots of the CEP17 in the nucleus. In addition, when an actual sample collected from a subject is used to determine whether pretreatment is appropriate, the determination of pretreatment appropriateness can be made based on bright spots of CEP17.

Also, the target site is not limited to nucleic acids, but may be substances other than cells on the cell surface and the like. Labeling of the target site is not limited to hybridization and also may be performed by antigen-antibody reaction. Further, the pretreatment part 20 may be configured to automatically perform processes such as centrifugation. The sample to be pretreated by the pretreatment part 20 is not limited to a blood sample, and may be, for example, a plasma sample or a sample collected from diseased tissue or the like. Cells to be analyzed are not limited to white blood cells, and may be, for example, epithelial cells.

What is claimed is:

1. A method for analyzing cells in a sample, comprising:
    treating a sample with a fluorescent label specifically binding to a target site of a cell;
    capturing fluorescence images of individual cells in the sample treated with the fluorescent label; and
    digitally analyzing at least some of the fluorescence images to identify at least a positive cell having a particular pattern of bright spots based on a color and a number of bright spots, wherein a positive cell is distinguishable from a negative cell according to the pattern of bright spots.

2. The method of claim 1, further comprising generating information of any one selected from a group consisting of: a number of positive cells, a number of negative cells, a ratio of the number of positive cells to the number of negative cells, and a ratio of the number of negative cells to the number of positive cells.

3. The method of claim 1, further comprising generating information of a population of positive cells in the sample.

4. The method of claim 1, wherein
a first image at a first wavelength and a second image at a second wavelength are captured, in the capturing; and
the method further comprising analyzing bright spots based on the first and second images.

5. The method of claim 1, further comprising acquiring an index that is indicative of an appropriateness of a pretreatment.

6. The method of claim 5, wherein the index is a ratio of a first number to a second number, the first number representing a number of detected cells through a flow cell and the second number representing a number of cells for which a fluorescent image is to be digitally analyzed.

7. The method of claim 5, wherein the index is a brightness of at least one bright spot.

8. The method of claim 5, wherein the index is a ratio between a brightness of at least one bright spot and a brightness of a background area of the cell.

9. The method of claim 5, wherein the index is a shape of at least one bright spot.

10. The method of claim 5, wherein the index is a size of at least one bright spot.

11. The method of claim 5, wherein the index is a number of bright spots.

12. The method of claim 5, further comprising displaying, on a display, that a pretreatment is appropriate when the index meets a criterion.

13. The method of claim 5, further comprising measuring a standard sample to acquire the index, and displaying information whether pretreatment is appropriate in reference to the acquired index.

14. The method of claim 1, further comprising
flowing the sample treated with the fluorescent label in a flow cell; and
irradiating cells in the sample running in the flow cell to excite fluorescence.

15. The method of claim 1, wherein the positive cell has a fusion of target gene.

16. A method for analyzing a sample, comprising:
hybridizing a nucleic acid of cells in a sample and a fluorescent-labeled probe;
irradiating the cells in the sample to excite fluorescence;
capturing fluorescence images of individual cells in the sample;
digitally analyzing at least some of the fluorescence images to extract bright spots in each individual cell of at least some of the individual cells; and
identifying, based on a number and a color of the bright spots, particular individual cells having a translocation of a target site.

17. The method of claim 16, wherein a number and a color of bright spots in the at least one of the fluorescence images varies according to a translocation of the target site.

18. The method of claim 16, further comprising generating information of a population of the particular cells in the sample.

19. A sample analyzer comprising:
a pretreatment device configured to treat a sample with a fluorescent label;
a light source configured to irradiate the sample treated with the fluorescent label;
an imaging device configured to capture fluorescence images of individual cells in the sample irradiated by light; and
a processor configured to digitally analyze at least some of the fluorescence images to identify at least a positive cell having a particular pattern of bright spots based on a color and a number of bright spots, wherein a positive cell is distinguishable from a negative cell according to the pattern of bright spots.

20. A method for analyzing a sample, comprising:
treating a sample with a fluorescent label specifically binding to a target site of a cell;
irradiating the sample treated with the fluorescent label;
capturing fluorescence images of individual cells in the sample;
digitally analyzing the fluorescence images to analyze bright spots in the individual cells to classify, based on a color and a number of the bright spots of the individual cells, the individual cells into at least two groups including positive cells and negative cells.

* * * * *